(12) United States Patent
Brereton et al.

(10) Patent No.: US 9,375,532 B2
(45) Date of Patent: Jun. 28, 2016

(54) AUTO-INJECTOR

(71) Applicant: SANOFI-AVENTIS DEUTSCHLAND GMBH, Frankfurt am Main (DE)

(72) Inventors: Simon Francis Brereton, Cambridgeshire (GB); Thomas Kemp, Hertfordshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/352,357

(22) PCT Filed: Oct. 11, 2012

(86) PCT No.: PCT/EP2012/070114
§ 371 (c)(1),
(2) Date: Apr. 17, 2014

(87) PCT Pub. No.: WO2013/057034
PCT Pub. Date: Apr. 25, 2013

(65) Prior Publication Data
US 2014/0243751 A1  Aug. 28, 2014

(30) Foreign Application Priority Data
Oct. 21, 2011 (EP) .................................... 11186233

(51) Int. Cl.
*A61M 5/20* (2006.01)
*A61M 5/32* (2006.01)
*A61M 5/315* (2006.01)

(52) U.S. Cl.
CPC ............ *A61M 5/2033* (2013.01); *A61M 5/3204* (2013.01); *A61M 5/3157* (2013.01); *A61M 5/326* (2013.01); *A61M 2005/206* (2013.01); *A61M 2005/208* (2013.01); *A61M 2205/581* (2013.01); *A61M 2205/582* (2013.01); *A61M 2205/583* (2013.01)

(58) Field of Classification Search
CPC ............ A61M 5/3232; A61M 5/3271; A61M 5/3219; A61M 5/3243; A61M 5/3204; A61M 5/2033; A61M 5/3157; A61M 2205/583; A61M 2205/582; A61M 2205/581; A61M 2005/208; A61M 2005/206; A61M 5/326
USPC ......... 604/198, 223, 210, 197, 207, 208, 209, 604/211, 339
See application file for complete search history.

(56) References Cited

U.S. PATENT DOCUMENTS 7,993,301 B2 * 8/2011 Boyd et al. ...................... 604/68
8,308,695 B2 * 11/2012 Laiosa .......................... 604/198

(Continued)

FOREIGN PATENT DOCUMENTS

| DE | 102007013836 | 9/2008 |
|----|--------------|--------|
| EP | 2399630 | 12/2011 |
| WO | 2009/063030 | 5/2009 |

OTHER PUBLICATIONS

International Search Report for Int. App. No. PCT/EP2012/070114, completed Jan. 7, 2013.

*Primary Examiner* — Kami A Bosworth
*Assistant Examiner* — Hamza Darb
(74) *Attorney, Agent, or Firm* — Fish & Richardson P.C.

(57) ABSTRACT

Described is an injection device for administering a dose of a medicament comprising a case having a proximal end and a distal end, a carrier adapted to accommodate a syringe, and a trigger button. In a first state, the trigger button is coupled to the case and/or the carrier and abuts the distal end of the case. In an intermediate state, the case moves proximally relative to the carrier and the trigger button, and the trigger button engages the carrier. In a second state, the trigger button and the carrier move proximally relative to the case, and the trigger button disengages the carrier and engages the case.

20 Claims, 28 Drawing Sheets

(56) References Cited

U.S. PATENT DOCUMENTS

2002/0095120 A1 7/2002 Larsen et al.
2009/0254036 A1 10/2009 Asmussen et al.
2013/0116625 A1* 5/2013 Holmqvist .................... 604/197

* cited by examiner

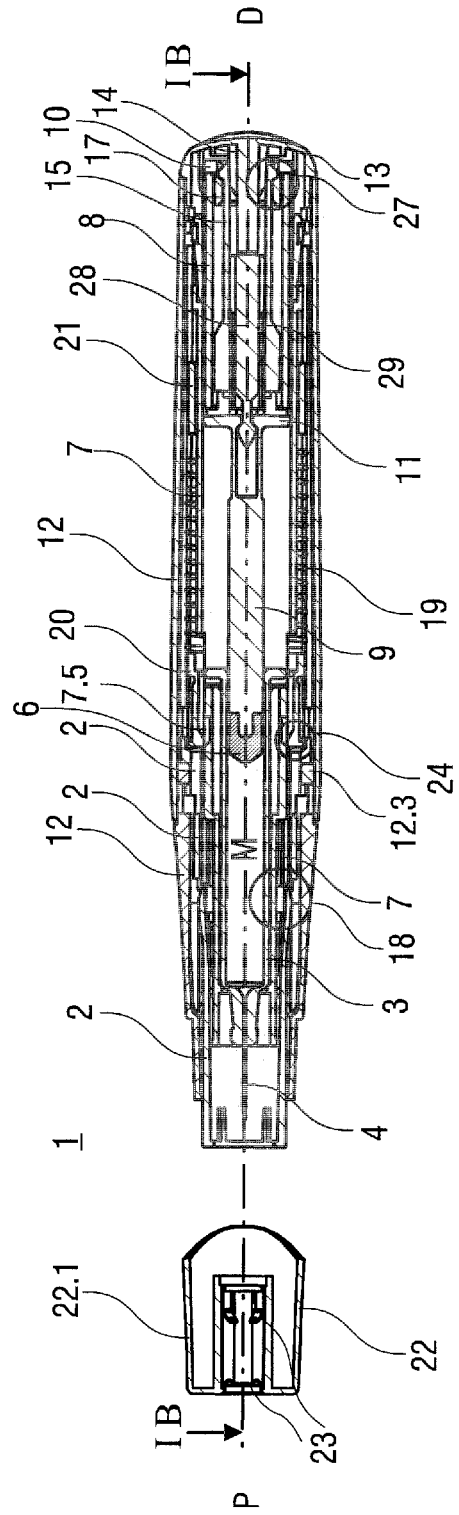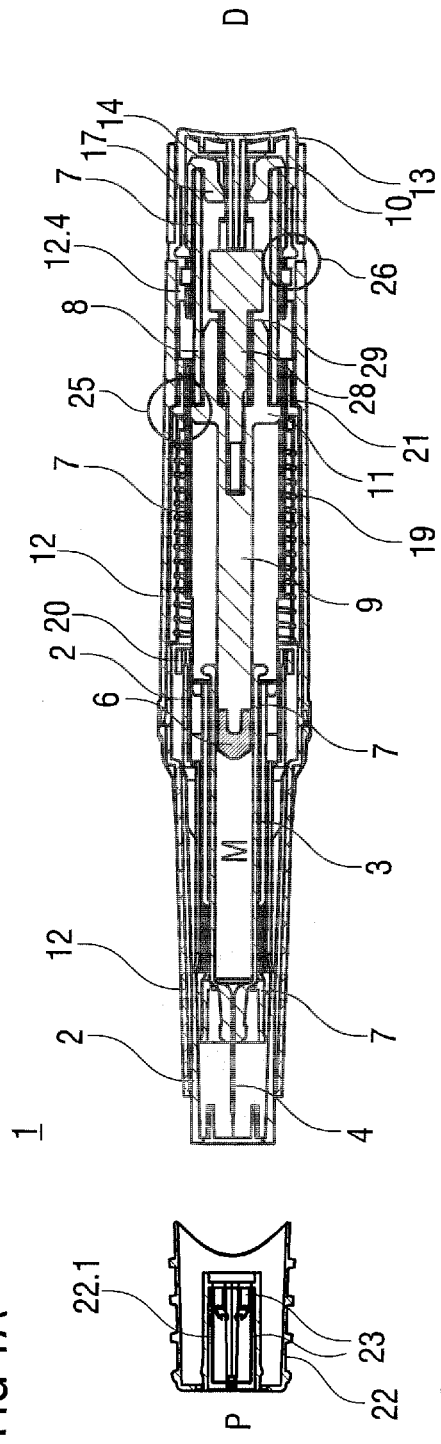
FIG 1A
FIG 1B

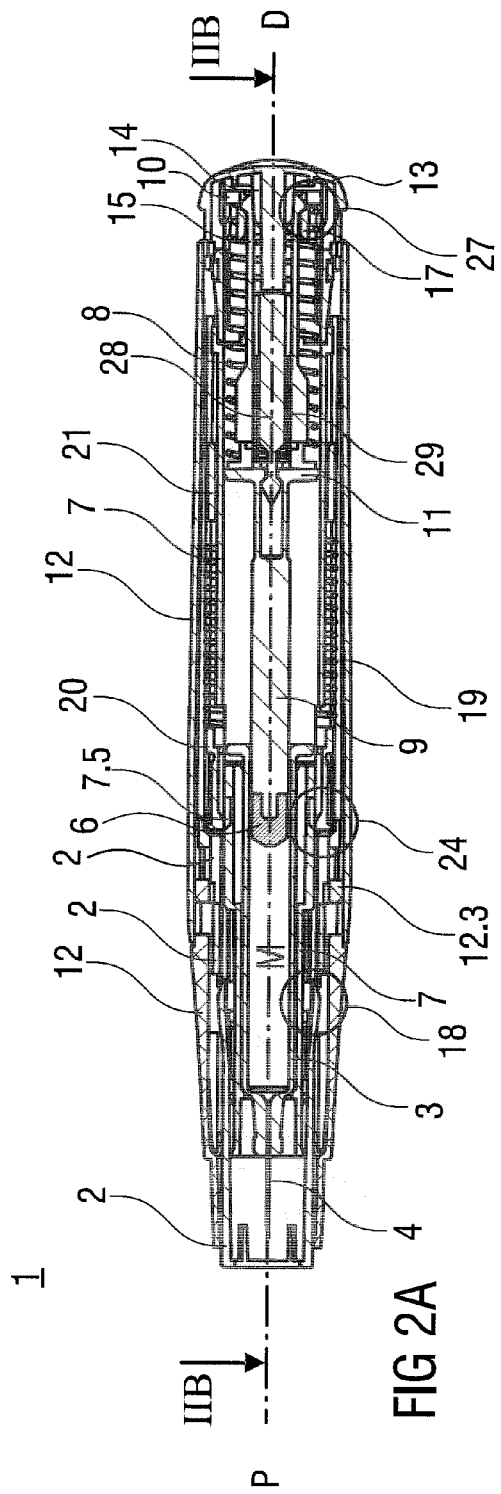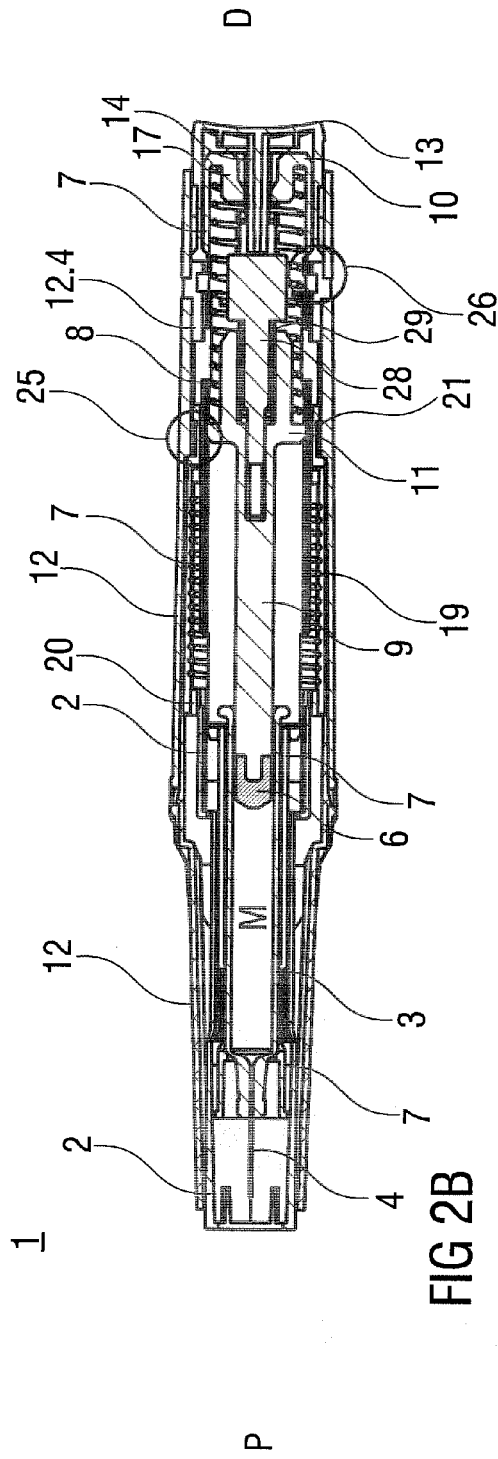

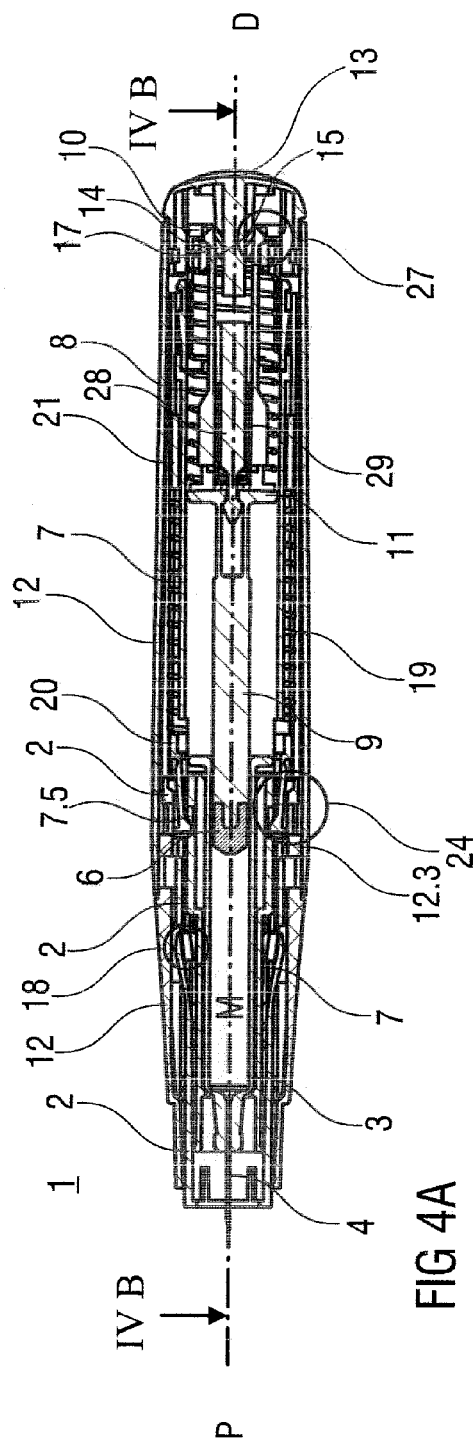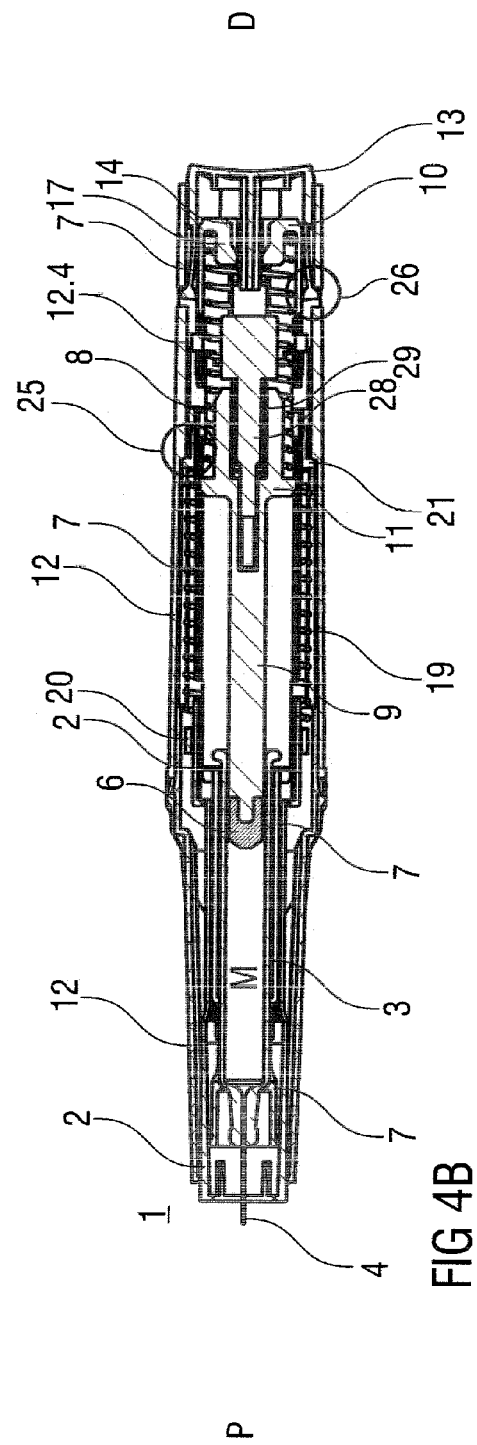
FIG 4A
FIG 4B

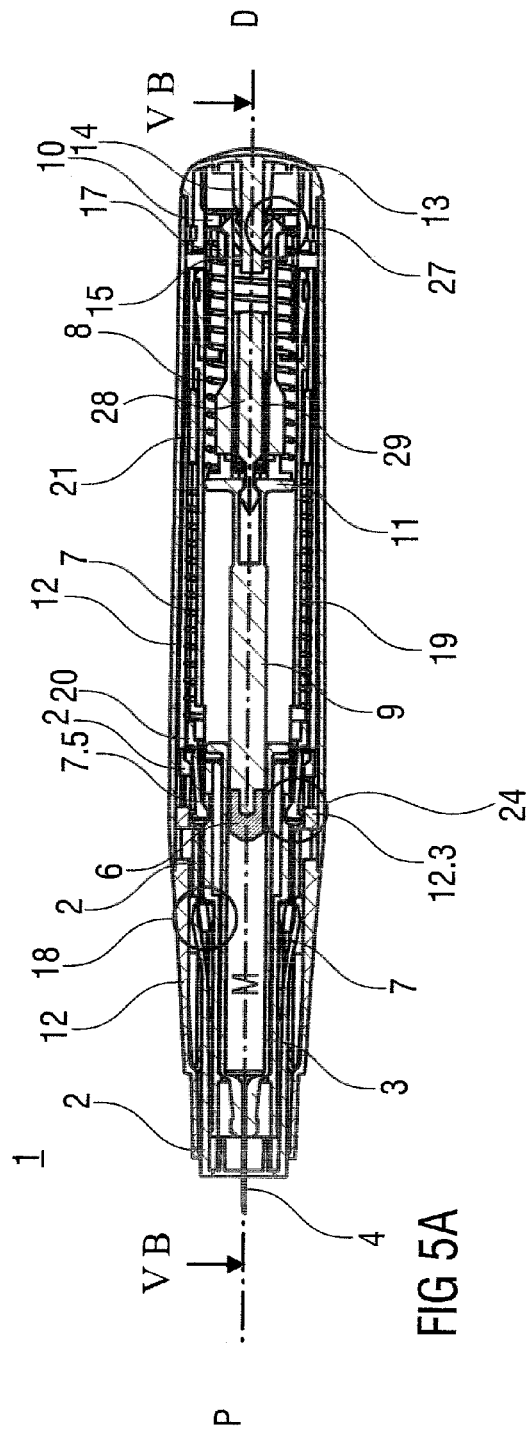
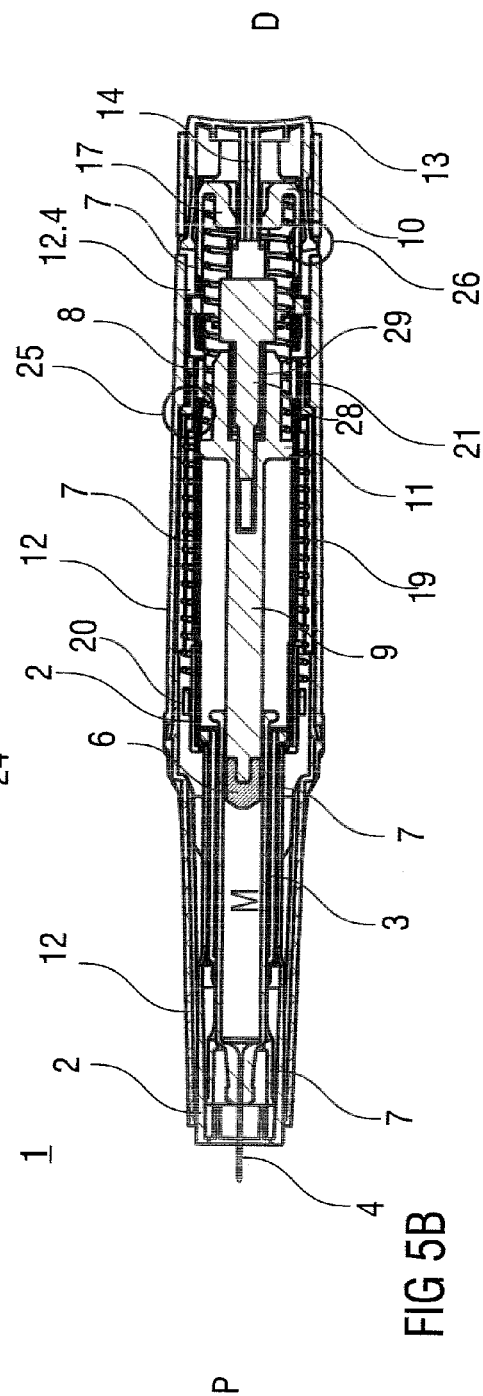
FIG 5A
FIG 5B

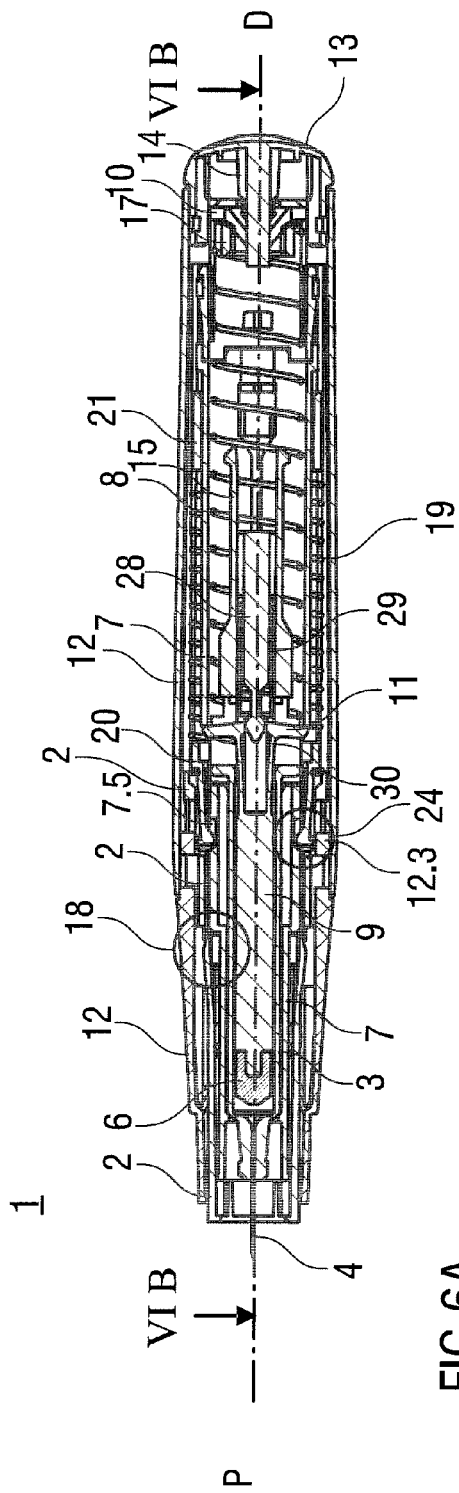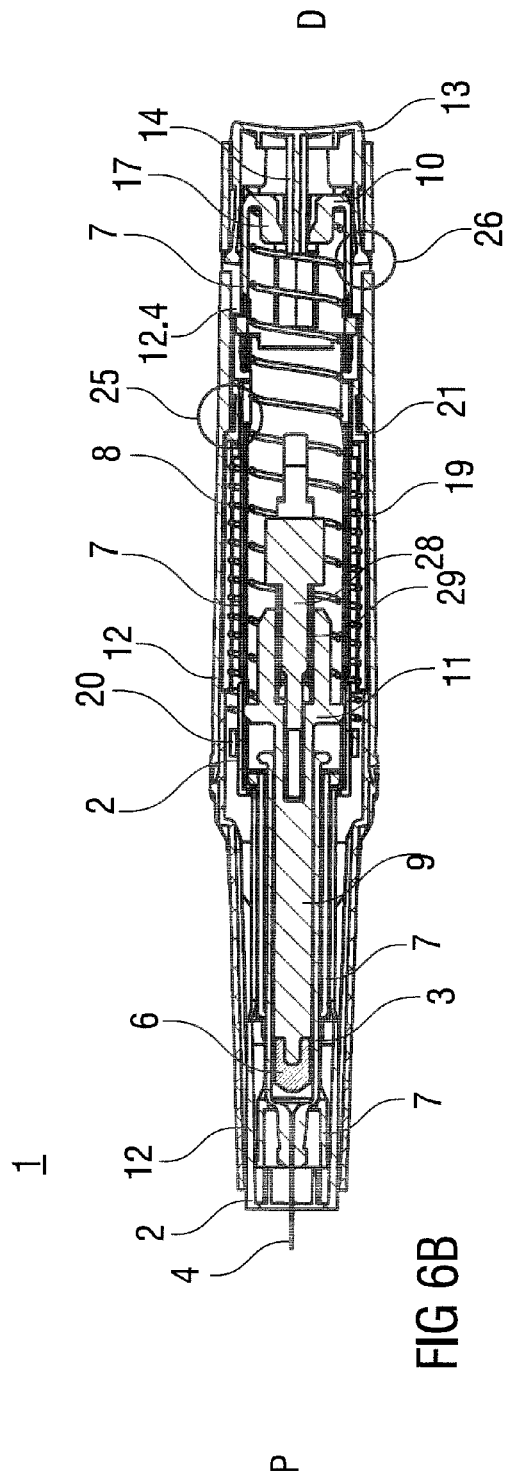

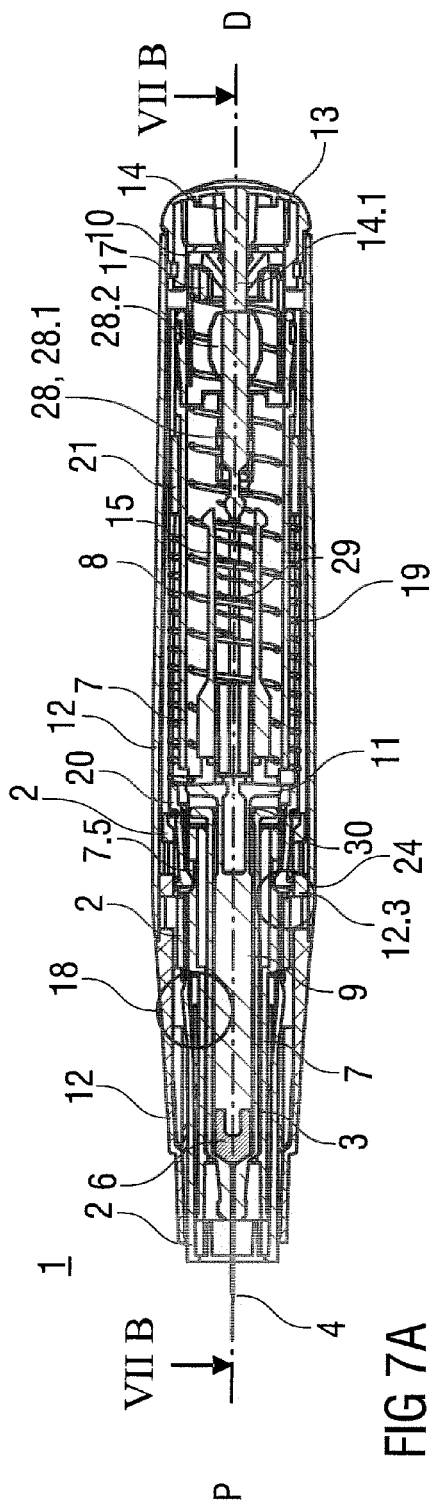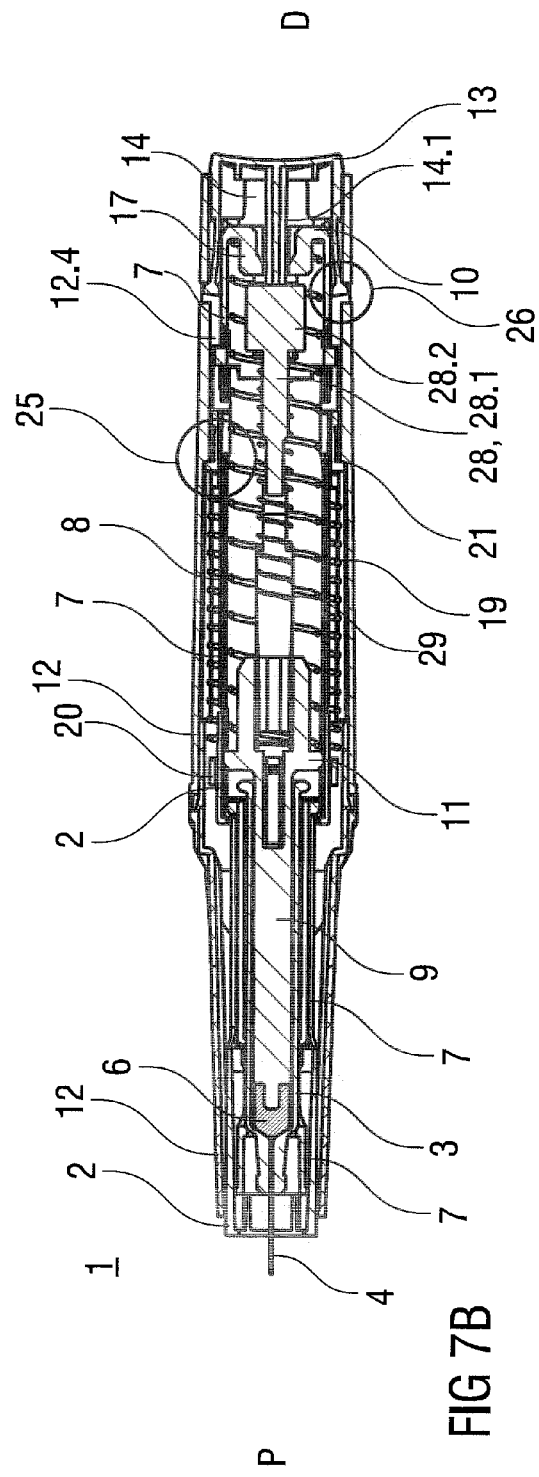

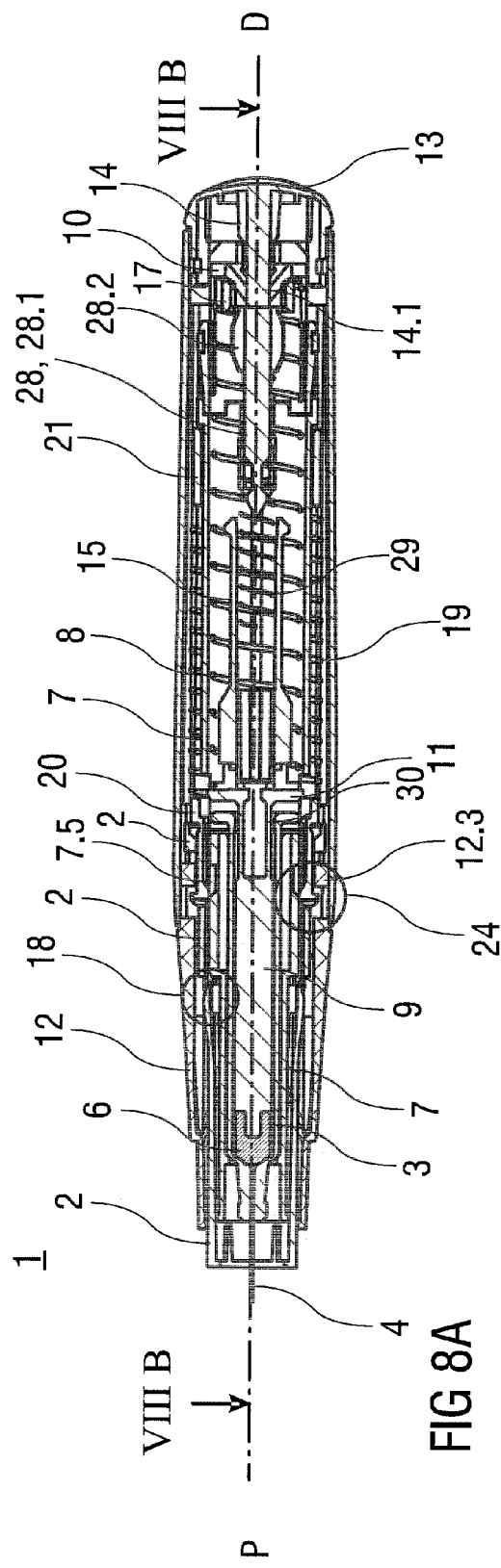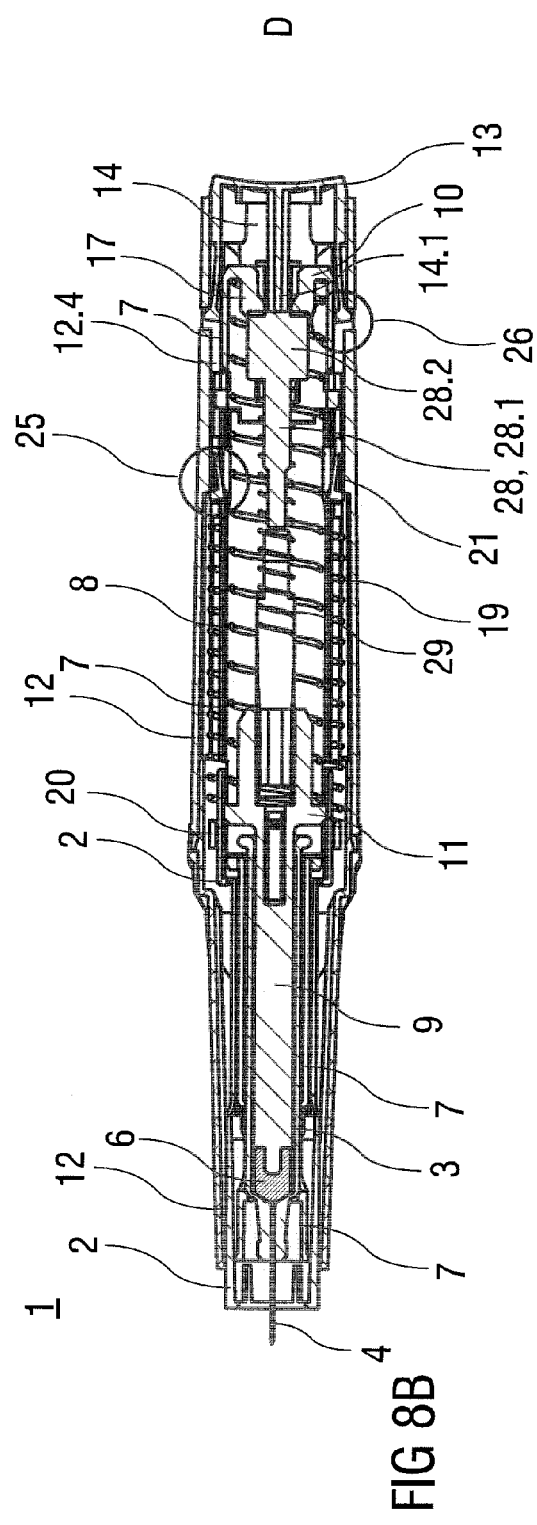
FIG 8A
FIG 8B

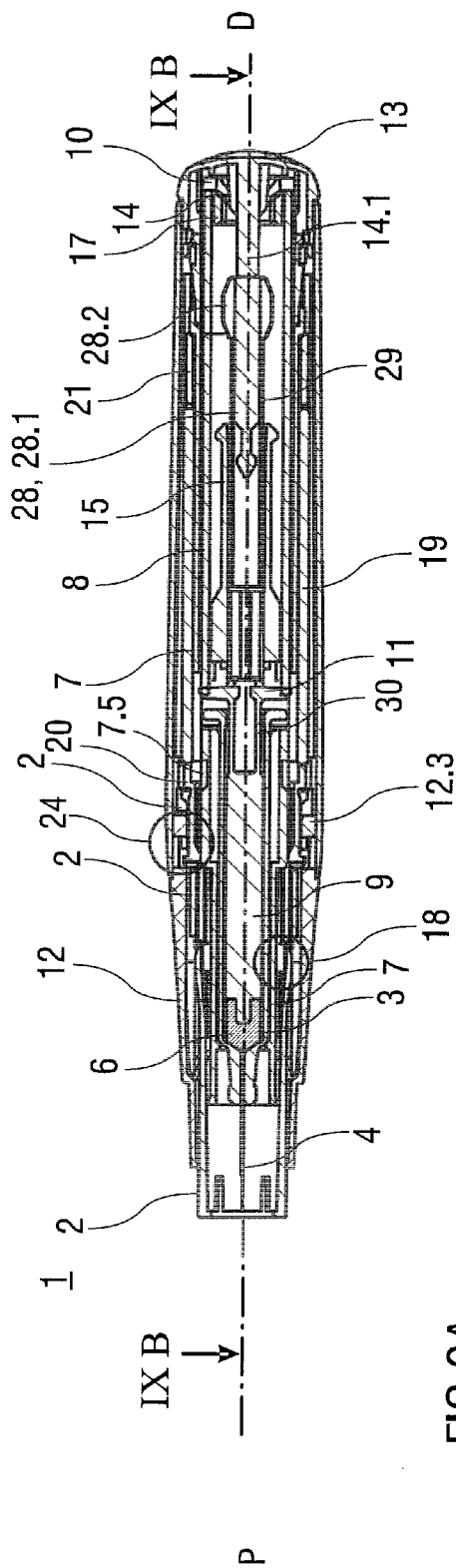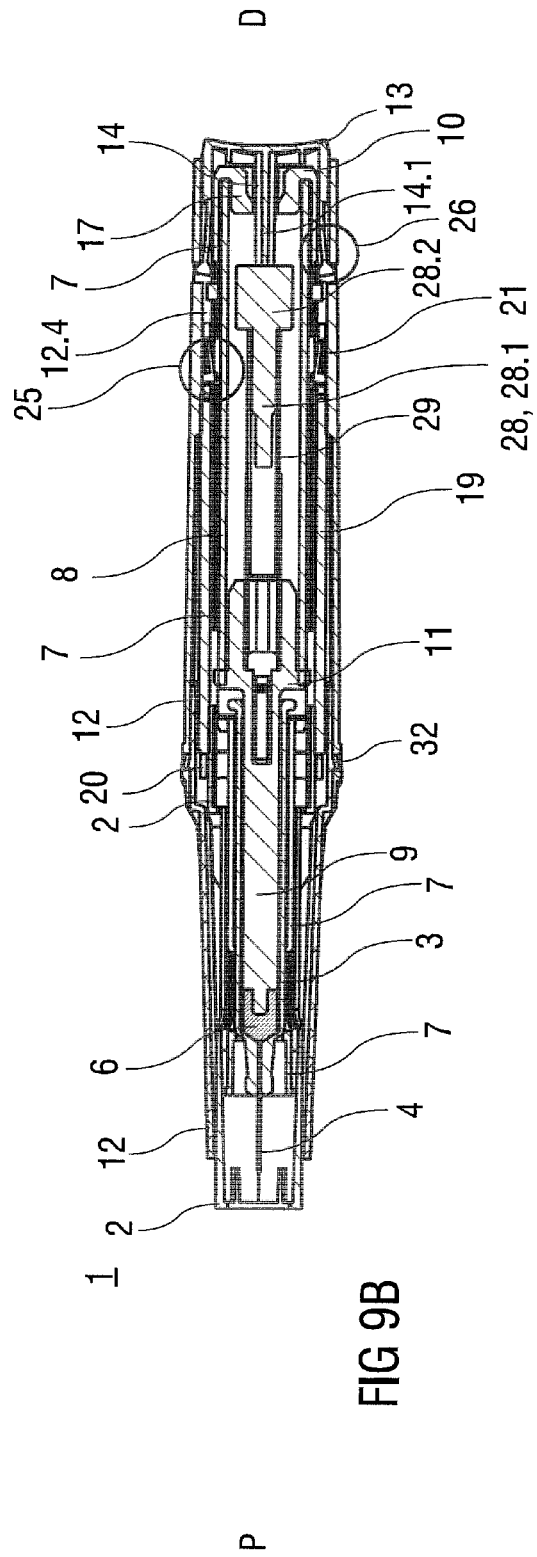
FIG 9A
FIG 9B

AUTO-INJECTOR

CROSS REFERENCE TO RELATED APPLICATIONS

The present application is a U.S. National Phase Application pursuant to 35 U.S.C. §371 of International Application No. PCT/EP2012/070114 filed Oct. 11, 2012, which claims priority to European Patent Application No. 11186233.0 filed Oct. 21, 2011. The entire disclosure contents of these applications are herewith incorporated by reference into the present application.

TECHNICAL FIELD

The invention relates to an auto-injector for administering a dose of a medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

High viscosity medicaments require high forces for expelling them through the relatively thin injection needle. To achieve these forces strong drive springs are needed. This can lead to a high impact felt by the user when inserting the needle into the skin and to high forces felt by the user when triggering the injection.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient. The term inwards refers to a radial direction pointing towards a longitudinal axis of the auto-injector whereas the term outwards refers to the opposite direction radially pointing away from the longitudinal axis.

In an exemplary embodiment, an injection device for administering a dose of a medicament comprises a case having a proximal end and a distal end, a carrier adapted to accommodate a syringe, and a trigger button. In a first state, the trigger button is coupled to the case and/or the carrier and abuts the distal end of the case. In an intermediate state, the case moves proximally relative to the carrier and the trigger button, and the trigger button engages the carrier. In a second state, the trigger button and the carrier move proximally relative to the case, and the trigger button disengages the carrier and engages the case.

In an exemplary embodiment, the trigger button includes a deflectable beam adapted to engage the case and the carrier. The case includes a case detent adapted to engage the beam. The beam includes a first ramp adapted to engage the case detent. The carrier includes a carrier detent adapted to engage the beam. The beam includes a second ramp adapted to engage the carrier detent. In the first state, the beam engages the case detent and/or the carrier detent. In the second state, the beam engages the case detent, and the beam abuts the carrier. In the intermediate state, the beam engages the carrier detent, and the beam abuts the case.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 shows two longitudinal sections of the auto-injector after removal of a cap and a protective needle sheath, FIG. 2 shows two longitudinal sections of the auto-injector with the case moved in proximal direction relative to the chassis, FIG. 4 shows two longitudinal sections of the auto-injector during needle advance, FIG. 5 shows two longitudinal sections of the auto-injector with the needle in an extended proximal position, FIG. 6 shows two longitudinal sections of the auto-injector during delivery of the medicament, FIG. 7 shows two longitudinal sections of the auto-injector with the stopper located in proximity of a proximal end of the syringe, FIG. 8 shows two longitudinal sections of the auto-injector with the case moved in the distal direction relative to the chassis after delivery, FIG. 9 shows two longitudinal sections of the auto-injector with the needle retracted into a needle safe position.

Corresponding parts are marked with the same reference symbols in all figures.

DETAILED DESCRIPTION

Figure 3A:
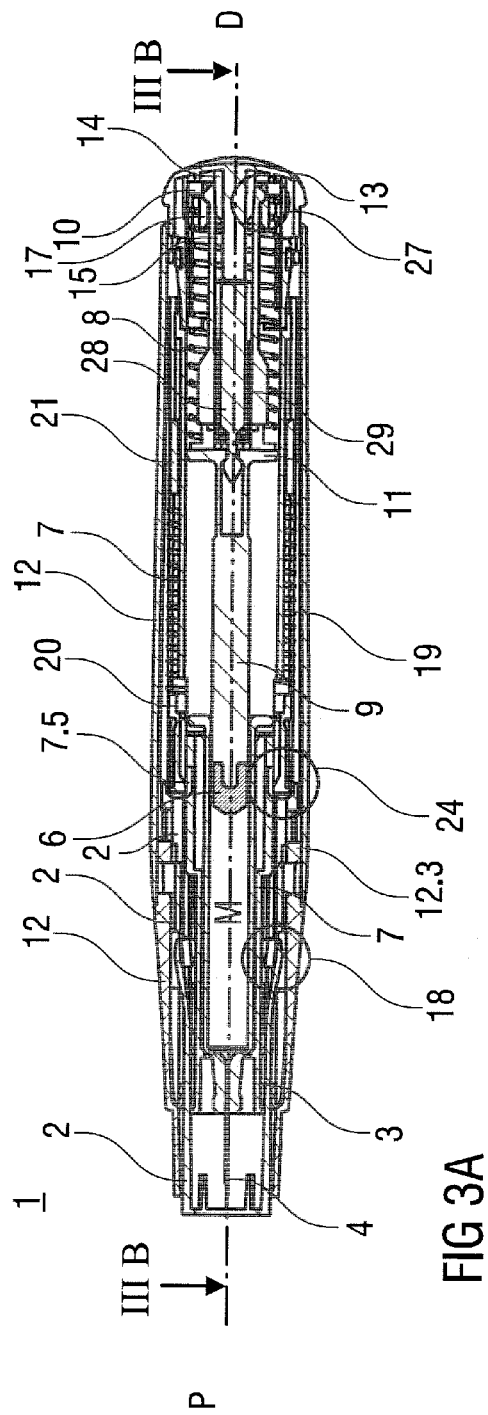
FIG. 3 shows two longitudinal sections of the auto-injector with a trigger button depressed.

A ramped engagement in the terminology of this specification is an engagement between two components with at least one of them having a ramp for engaging the other component in such a manner that one of the components is flexed aside when the components are axially pushed against each other provided this component is not prevented from flexing aside.

FIGS. 1a and 1b show two longitudinal sections of an auto-injector 1 in different section planes, the different section planes approximately 90° rotated to each other, wherein the auto-injector 1 is in an initial state prior to starting an injection. The auto-injector 1 comprises a chassis 2. In the following the chassis 2 is generally considered as being fixed in position so motion of other components is described relative to the chassis 2. A syringe 3, e.g. a Hypak syringe, with a hollow injection needle 4 is arranged in a proximal part of the auto-injector 1. When the auto-injector 1 or the syringe 3 is assembled a protective needle sheath (not illustrated) is attached to the needle 4. A stopper 6 is arranged for sealing the syringe 3 distally and for displacing a medicament M through the hollow needle 4. The syringe 3 is held in a tubular carrier 7 and supported at its proximal end therein. The carrier 7 is slidably arranged in the chassis 2.

A drive spring 8 in the shape of a compression spring is arranged in a distal part of the carrier 7. A plunger 9 serves for forwarding the force of the drive spring 8 to the stopper 6.

The drive spring 8 is loaded between a distal carrier end face 10 of the carrier 7 and a thrust face 11 arranged distally on the plunger 9.

The carrier 7 is a key element housing the syringe 3, the drive spring 8 and the plunger 9, which are the components required to eject the medicament M from the syringe 3. These components can therefore be referred to as a drive sub-assembly.

Figure 14A:
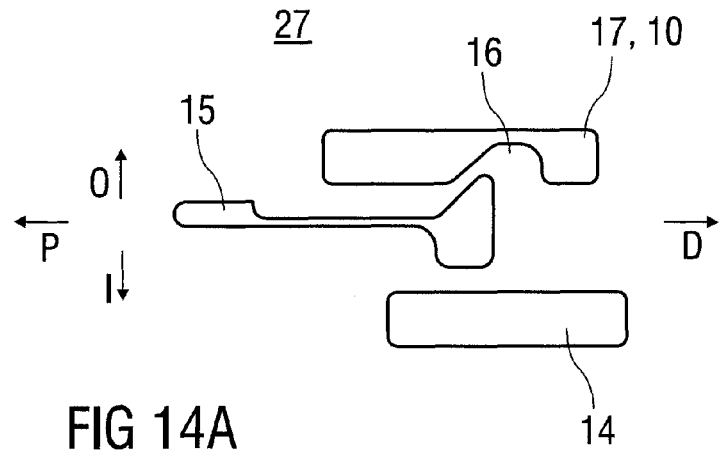
FIG. 14 shows schematic views of a plunger release mechanism in three different states.

The chassis 2 and the carrier 7 are arranged within a tubular case 12. A trigger button 13 is arranged at a distal end of the case 12. In a plunger release mechanism 27 a peg 14 protrudes from a distal end face of the trigger button 13 in the proximal direction P between two resilient arms 15 originating and distally extending from the thrust face 11 of the plunger 9 within the drive spring 8 thus preventing them from flexing towards each other in an initial state A illustrated in FIG. 14A. In FIG. 14A only one of the resilient arms 15 is shown to illustrate the principle. Outwardly the resilient arms 15 are caught in respective first recesses 16 in a distal carrier sleeve 17 attached distally to the distal carrier end face 10 and arranged inside the drive spring 8. The engagement of the resilient arms 15 in the first recesses 16 prevents axial translation of the plunger 9 relative to the carrier 7. The resilient arms 15 are ramped in a manner to flex them inwards on relative motion between the plunger 9 and the carrier 7 under load of the drive spring 8, which is prevented by the peg 14 in the initial state A.

The carrier 7 is locked to the chassis 2 for preventing relative translation by a detent mechanism 18 illustrated in more detail in FIGS. 10A to 10D.

Figure 15A:
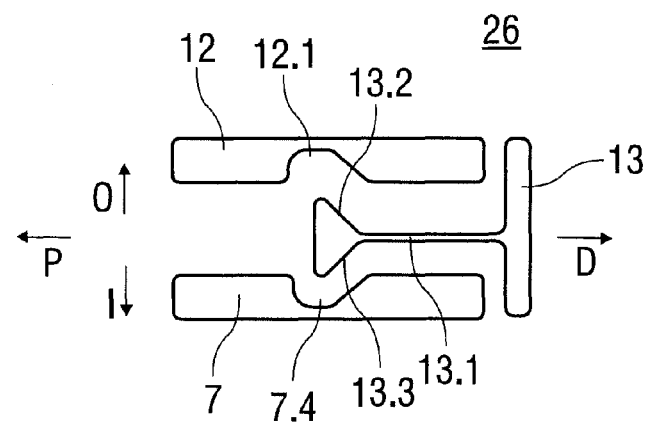
FIG. 15 shows schematic views of a button release mechanism in three different states.

The trigger button 13 is initially engaged to the case 12 by a button release mechanism 26 and cannot be depressed. The button release mechanism 26 is illustrated in detail in FIGS. 15A to 15C. Referring now to FIG. 15A the button release mechanism 26 comprises a resilient proximal beam 13.1 on the trigger button 13, the proximal beam 13.1 having an outward first ramp 13.2 and an inward second ramp 13.3. In a first state A illustrated in FIG. 15A the inward second ramp 13.3 is engaged in a ramped carrier detent 7.4 of the carrier 7 preventing the trigger button 13 from moving out of the distal end D. The trigger button 13 proximally abuts both the case 12 and the carrier 7 hence being prevented from being depressed in the proximal direction P.

Referring again to FIGS. 1A and 1B a control spring 19 in the shape of another compression spring is arranged around the carrier 7 and acts between a proximal first collar 20 and a distal second collar 21. The control spring 19 is used to move the carrier 7 and hence the drive sub-assembly in the proximal direction P for needle extension or in the distal direction D for needle retraction.

Prior to the state as shown in FIGS. 1A and 1B a cap 22 is attached to the proximal end of the case 12 and the protective needle sheath is still in place over the needle 4 and the needle hub. An inner sleeve 22.1 of the cap 22 is arranged inside the chassis 2 and over the protective needle sheath. In the inner sleeve 22.1 a barb 23 is attached. The barb 23 is engaged to the protective needle sheath for joint axial translation.

Figure 10A:
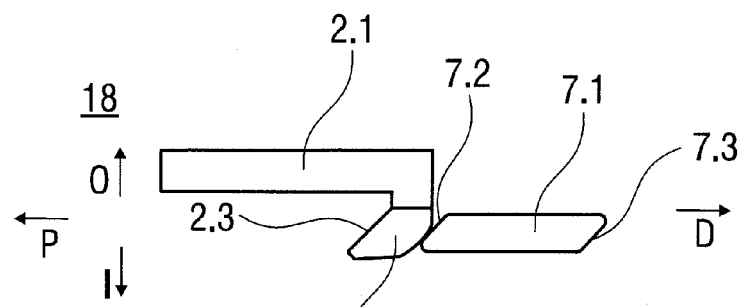
FIG. 10 shows schematic views of a detent mechanism for controlling movement of a carrier relative to a chassis of the auto-injector in four different states.

A sequence of operation of the auto-injector 1 is as follows:

A user pulls the cap 22 from the proximal end of the case 12. The barb 23 joins the protective needle sheath to the cap 22. Hence, the protective needle sheath is also removed on removal of the cap 22. FIGS. 1A and 1B show the auto-injector 1 with the cap 22 and needle sheath removed. The carrier 7 and syringe 3 are prevented from moving in the proximal direction P by the detent mechanism 18 being in a state A as in FIG. 10A. Referring now to FIG. 10A, the detent mechanism 18 comprises a resilient beam 2.1 on the chassis 2 with an inwardly protruding first beam head 2.2. The first beam head 2.2 has a proximal third ramp 2.3. The detent mechanism 18 further comprises a rhomboid ramp member 7.1 on the carrier 7 having a proximal fourth ramp 7.2 and a distal fifth ramp 7.3. In state A a rounded off distal side of the first beam head 2.2 abuts the ramp member 7.1 in the distal direction D resisting movement of the carrier 7 in the proximal direction P relative to the chassis 2. A rib on the case 12 is provided for preventing outward deflection of the resilient beam 2.1 thereby also preventing motion of the carrier 7 relative to the chassis 2.

Figure 11A:
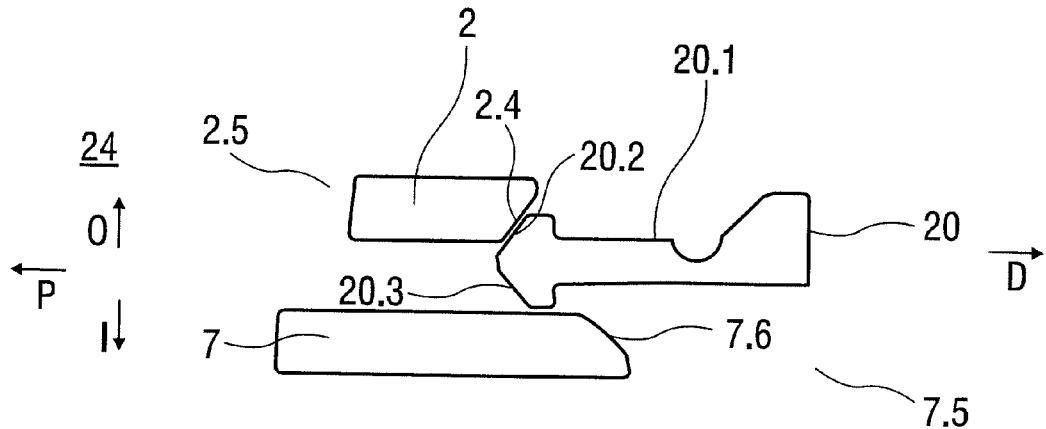
FIG. 11 shows schematic views of a needle extension control mechanism for controlling movement of a first collar in six different states.

Referring again to FIGS. 1A and 1B the user grabs the case 12 and places the chassis 2 protruding from the case 12 at the proximal end P against an injection site, e.g. a patient's skin. As the auto-injector 1 is pressed against the injection site the case 12 translates in the proximal direction P relative to the chassis 2 into an advanced position as illustrated in FIGS. 2A and 2B. The second collar 21 is locked to the case 12 and is moved with the case 12 relative to the chassis 2 and relative to nearly all other components of the auto-injector 1 thus slightly compressing the control spring 19 against the first collar 20 which is prevented from moving in the proximal direction P by the chassis 2 due to a needle extension control mechanism 24 being in a state A illustrated in detail in FIG. 11A. Referring now to FIG. 11A, a resilient member in the shape of an arrowhead 20.1 is proximally arranged on the first collar 20. The first collar 20 with the arrowhead 20.1 is being forced in the proximal direction P under load of the compressed control spring 19. An outward sixth ramp 20.2 on the arrowhead 20.1 interacts with a second distal seventh ramp 2.4 on the chassis 2 ramping the arrowhead 20.1 in an inward direction I which is prevented by the arrowhead 20.1 inwardly abutting the carrier 7. Hence, the first collar 20 cannot translate in the proximal direction P.

The arrowhead 20.1 may have a different geometry than in FIGS. 11A to 11F, such as the rounded off arrowhead 20.1 in FIGS. 1 to 9. The function of the arrowhead 20.1 is not affected by this variant.

Figure 12A:
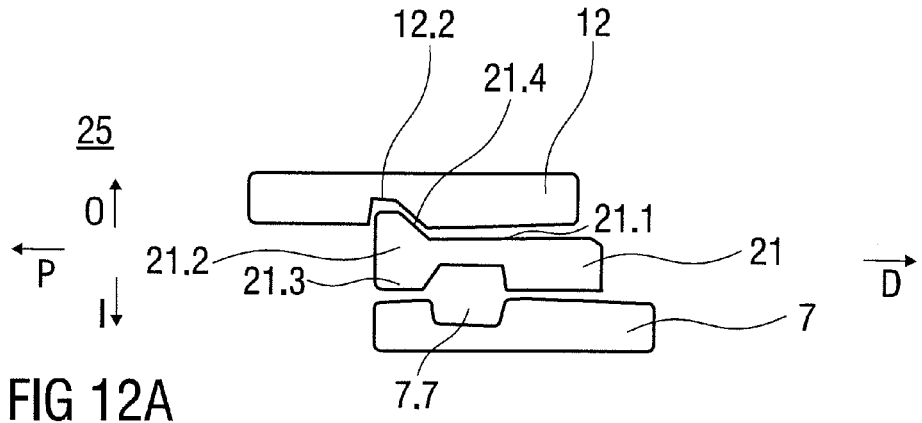
FIG. 12 shows schematic views of a syringe retraction control mechanism in three different states

Referring again to FIGS. 2A and 2B the second collar 21 is locked to the case due to a syringe refraction control mechanism 25 being in a state A illustrated in detail in FIG. 12A. Referring now to FIG. 12A, the syringe retraction control mechanism 25 comprises a resilient proximal beam 21.1 on the second collar 21, the proximal beam 21.1 having a second beam head 21.2 having an inward boss 21.3 and a distal outward eighth ramp 21.4. The distal outward eighth ramp 21.4 is engaged in a ramped second case detent 12.2 in a manner ramping the second beam head 21.1 in the inward direction I with the second collar 21 under load of the control spring 19 in the distal direction D which is prevented by the inward boss 21.3 inwardly abutting the carrier 7.

Referring again to FIGS. 2A and 2B, if the user was to move the case 12 away from the injection site, the control spring 19 expands returning the auto-injector 1 to the initial condition after removal of the cap 22 as illustrated in FIGS. 1A and 1B.

In the state as in FIGS. 2A and 2B the carrier 7 continues to be prevented from moving in the proximal direction P by the detent mechanism 18, however with the case 12 in its advanced position the detent mechanism 18 is unlocked as the rib on the case 12 has also moved and no longer prevents outward deflection of the resilient beam 2.1. Movement of the case 12 relative to the carrier 7, which is locked to the chassis 2 by the detent mechanism 18, causes the button release mechanism 26 to switch to an intermediate state B illustrated in FIG. 15B. As the case 12 is moved the trigger button 13 remains abutted against the carrier 7 with the inward second ramp 13.3 on the proximal beam 13.1 engaged in a ramped carrier detent 7.4 arranged in the carrier 7. As the case 12 is translated further in the proximal direction P it supports the proximal beam 13.1 outwardly thus locking the trigger button 13 to the carrier 7. The trigger button 13 now protrudes from the distal end D of the case 12 and is ready to be pressed.

Figure 10B:
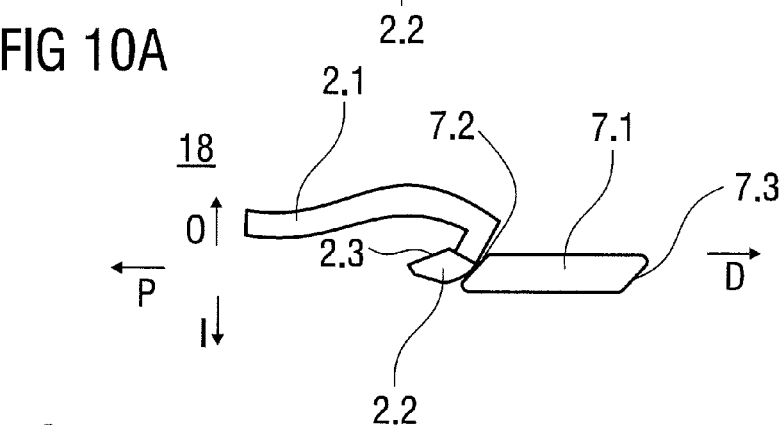
Figure 10C:
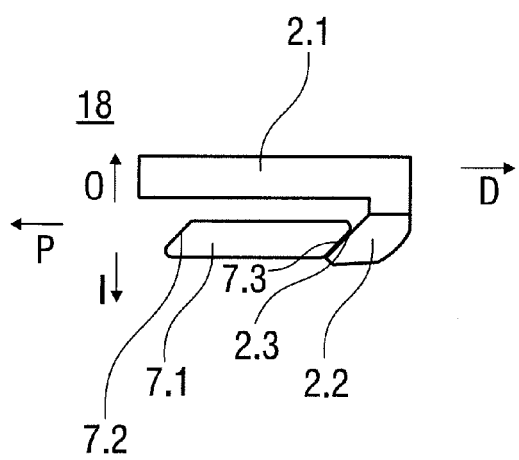

In the state as in FIGS. 2A and 2B the user depresses the trigger button 13 in the proximal direction P. As the trigger button 13 abuts against the carrier 7 the carrier 7 is pushing in the proximal direction P against the chassis 2, the carrier 7 and the chassis 2 interacting in the detent mechanism 18. The force exerted by the user pressing the trigger button 13 is resolved through the chassis 2 onto the injection site, not between the trigger button 13 and the case 12. The detent mechanism 18 provides a resistive force when the user pushes the trigger button 13. Once the user applies a force which exceeds a pre-determined value the detent mechanism 18 releases, initiating the injection cycle. Referring now to FIG. 10B showing the detent mechanism 18 in a state B, the resilient beam 2.1 on the chassis 2 begins to bow under load from the rhomboid ramp member 7.1 on the carrier 7, storing elastic energy. Despite the proximal fourth ramp 7.2 on the ramp member 7.1 friction between the contacting faces of the first beam head 2.2 and the proximal fourth ramp 7.2 prevents movement of the first beam head 2.2 in the outward direction O until the straightening force in the resiliently deformed beam 2.1 is sufficiently large to overcome it. At this point the resilient beam 2.1 is deflected in the outward direction O moving out of the way of the carrier 7 thus allowing the carrier 7 to translate in the proximal direction P. When the carrier 7 travels sufficiently far in the proximal direction P the rhomboid ramp member 7.1 on the carrier 7 passes under the first beam head 2.2 thus allowing it to relax and move back in the inward direction I distally behind the rhomboid ramp member 7.1 in a state C illustrated in FIG. 10C at the same time constraining translation of the carrier 7 in the distal direction D relative to the chassis 2.

Figure 11B:
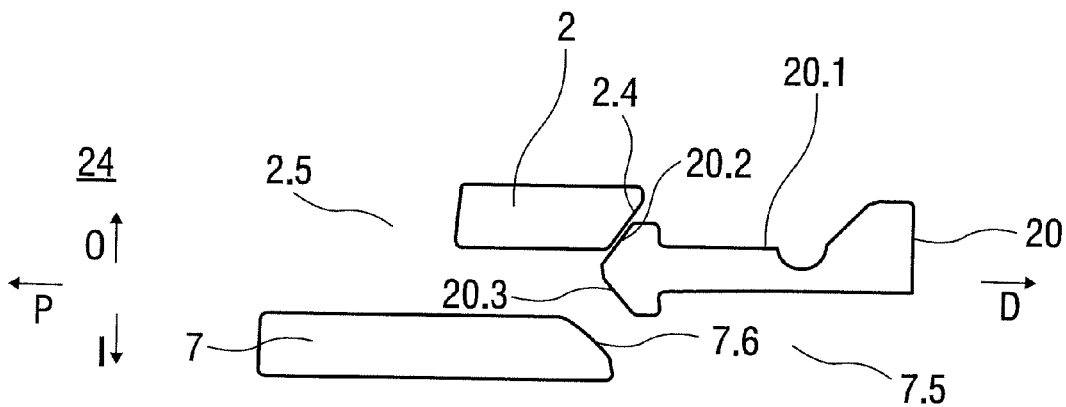
Figure 11C:
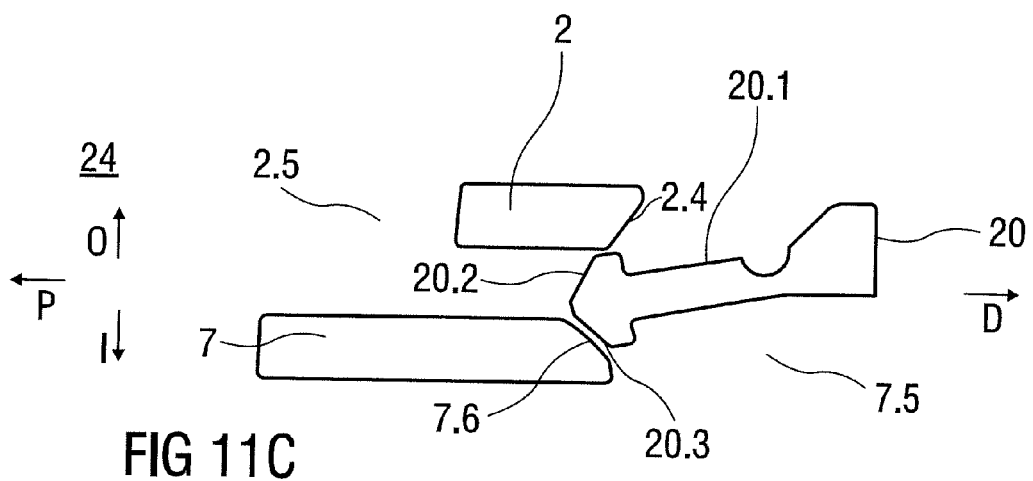

Once the carrier 7 slides far enough in the proximal direction P relative to the first collar 20 the needle extension control mechanism 24 is switched to a state B as illustrated in FIG. 11B. In FIG. 11B the carrier 7 has been translated in the proximal direction P in such a manner that the arrowhead 20.1 on the first collar 20 is no longer inwardly supported. This may be achieved by a second recess 7.5 in the carrier 7. The arrowhead 20.1 is now deflected in the inward direction I into the second recess 7.5 under load of the control spring 19 arriving at a state C as illustrated in FIG. 11C. The first collar 20 is now decoupled from the chassis 2. Instead, the arrowhead 20.1 couples the first collar 20 to the carrier 7 by an inward ninth ramp 20.3 engaging a distal tenth ramp 7.6 on the carrier 7 at the proximal end of the second recess 7.5. Hence, the control spring 19 continues moving the carrier 7 in the proximal direction P from this point. Whilst the user advances the needle 4 by a proportion of its travel, the control spring 19 takes over insertion before the needle 4 protrudes from the proximal end P. Therefore the user experience is that of pressing a button, rather than manually inserting a needle.

The detent mechanism 18 relies on the user applying a force rather than a displacement. Once the force applied exceeds the force required to switch the detent the user will push the trigger button 13 fully, ensuring that the first collar 20 will always switch. If the user fails to pass the detent, the trigger button 13 returns to its unused state ready for use as illustrated in FIGS. 2A and 2B. This feature avoids the auto-injector 1 arriving in an undefined state.

Figure 3B:
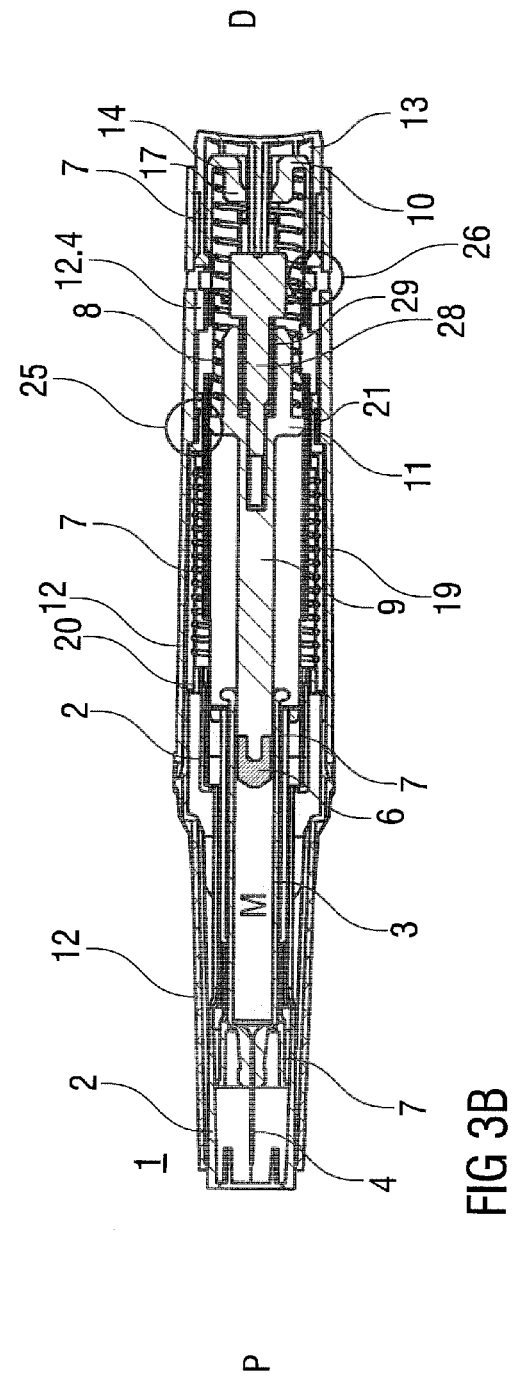

FIGS. 3A and 3B show the auto-injector 1 with the trigger button 13 depressed sufficiently for the control spring 19 to couple on to the carrier 7 and continue moving the carrier 7 forwards, but not yet abutting the case 12.

The carrier 7 coupled to the first collar 20 is translated in the proximal direction P driven by the control spring 19. As the syringe 3 is arranged for joint axial translation with the carrier 7 the syringe 3 and needle 4 are also translated resulting in the needle 4 protruding from the proximal end P and being inserted into the injection site. The trigger button 13 returns to its initial position relative to the case 12 whereby the proximal beam 13.1 is deflected in the outward direction O by the inward second ramp 13.3 engaging a ramp in the carrier detent 7.4, hence the proximal beam 13.1 deflects into the first case detent 12.1 and latches to the case 12 from the carrier 7. The carrier 7 translates further in the proximal direction P preventing inward deflection of the proximal beam 13.1 so the outward first ramp 13.2 cannot disengage from the first case detent 12.1.

Figure 14B:
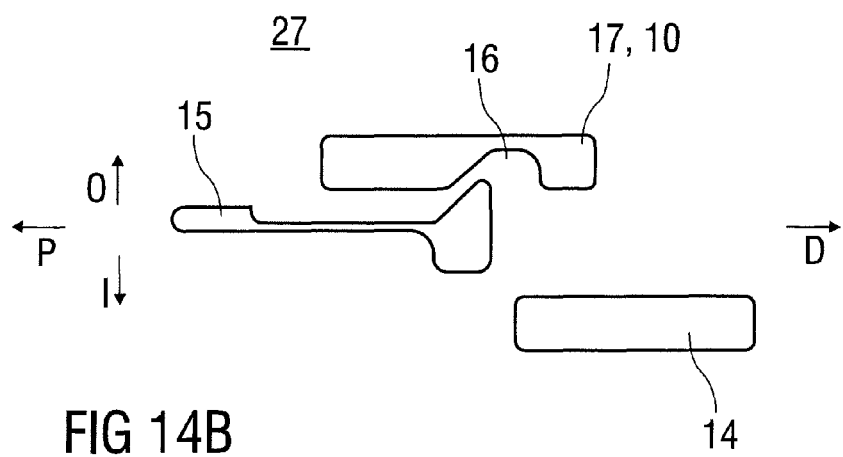
Figure 14C:
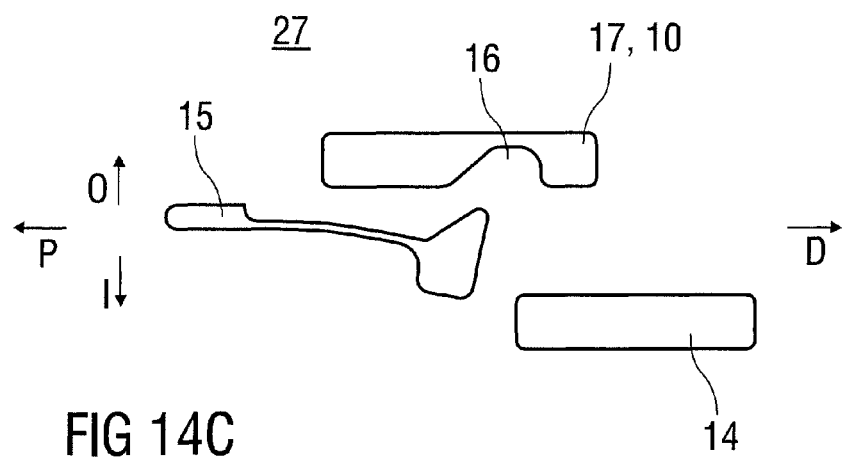

Immediately prior to the needle 4 reaching full insertion depth as illustrated in FIGS. 4A and 4B the peg 14 on the trigger button 13 is pulled out from between the resilient arms 15 on the carrier 7 sufficiently to allow inward deflection of the resilient arms 15. Hence, the plunger release mechanism 27 arrives in a state B shown in FIG. 14B with the resilient arms 15 no longer inwardly supported by the peg 14. Due to the ramped engagement of the resilient arms 15 in the first recess 16 they are deflected in the inward direction I under load of the drive spring 8 arriving in a state C illustrated in FIG. 14C. Hence, the plunger 9 is released from the carrier 7 and driven in the proximal direction P by the drive spring 8, ready to expel the medicament M. The force to pull the peg 14 out from between the resilient arms 15 is provided by the control spring 19 while the force required to deflect the resilient arms 15 out of engagement to the carrier 7 is provided by the drive spring 8.

While the plunger 9 moves and closes a gap to the stopper 6 the movement of the carrier 7 in the proximal direction P is completed by the control spring 19 pushing the first collar 20.

Figure 11D:
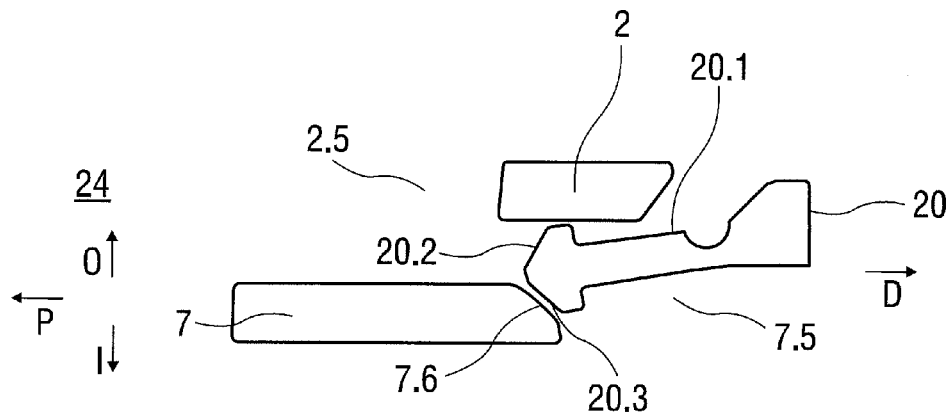

As the carrier 7 moves with respect to the chassis 2 during needle extension the needle extension mechanism 24 arrives in a state D illustrated in FIG. 11D. The arrowhead 20.1 has moved with the carrier 7 and is still kept inwardly deflected by the chassis 2 thus preventing the first collar 20 from disengaging the carrier 7. The arrowhead 20.1 must be able to deflect in the outward direction O to allow retraction which will be discussed below. In order to allow outward deflection the arrowhead 20.1 travels proximally beyond the part of the chassis 2 shown in FIGS. 11A to 11F next to an aperture 2.5 in the chassis 2. However, as long as the case 12 is being kept pressed against the injection site and not allowed to return in the distal direction D beyond a predefined distance under load of the control spring 19 the arrowhead 20.1 will be kept from deflecting in the outward direction O by a first rib 12.3 on the case 12 (not illustrated in FIGS. 11A to 11F, see FIGS. 4A to 7A) during about the second half of its motion for needle extension.

The needle 4 is now fully inserted into the injection site as illustrated in FIGS. 5A and 5B. The time between the trigger button 13 pressed and the needle 4 being fully inserted is very short, however several mechanical operations take place in this time. The needle extension depth is defined by the carrier 7 relative to the chassis 2 not relative to the case 12, so if the user flinches or fails to hold the auto-injector 1 hard against the skin, only the case 12 will move in the distal direction D while the injection depth remains constant.

As soon as the plunger 9 has closed the gap to the stopper 6 under force of the drive spring 8 the stopper 6 is pushed in the proximal direction P within the syringe 3 displacing the medicament M through the needle 4.

Immediately prior to the end of expelling the medicament with the stopper 6 having almost bottomed out in the syringe 3 as illustrated in FIGS. 6A and 6B a feedback component 28 is released. The stack up of tolerances, most notably due to the syringe 3 requires that the feedback must always be released prior to fully expelling the medicament. Otherwise, with certain combinations of parts, the feedback would not always release. The feedback component 28 comprises an elongate portion 28.1 arranged between the resilient arms 15 on the plunger 9 and a distal end portion 28.2 arranged to abut a proximal extension 14.1 on the peg 14 of the trigger button 13. Two second resilient arms 30 originate from the plunger 9 and extend in the distal direction D. A feedback spring 29 is arranged to bias the feedback component 28 in the distal direction D relative to the plunger 9 by proximally bearing against a rib on the plunger 9 and distally against the distal end portion 28.2 of the feedback component 28.

Figure 13A:
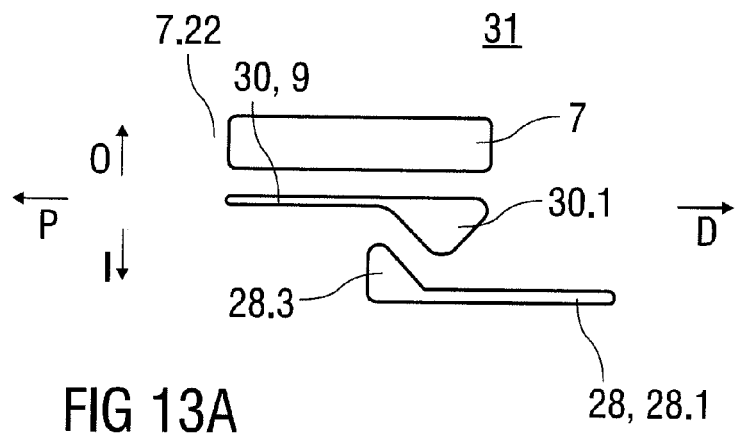
FIG. 13 shows schematic views of a feedback release mechanism for indicating the end of injection in three different states.
Figure 13B:
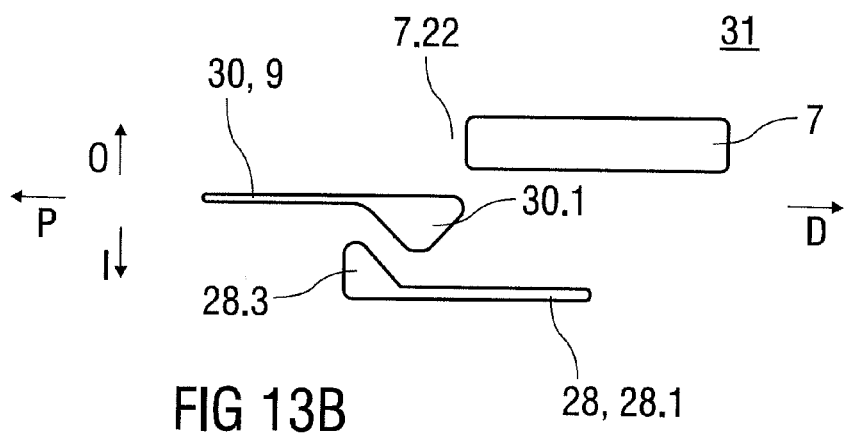
Figure 13C:
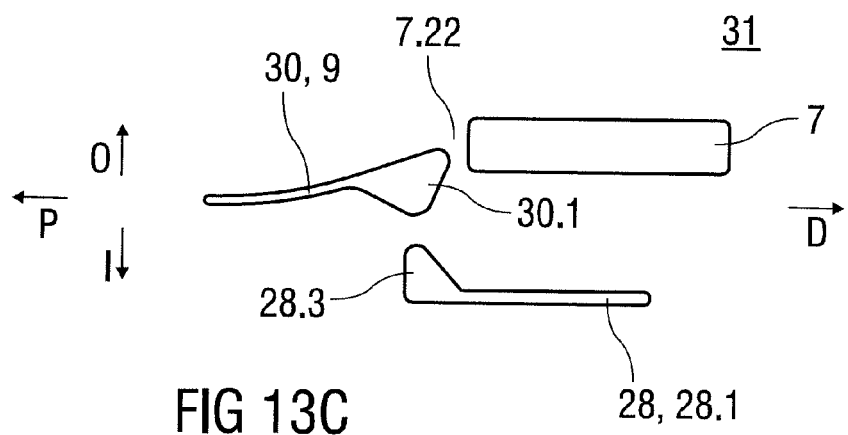
Figure 15B:
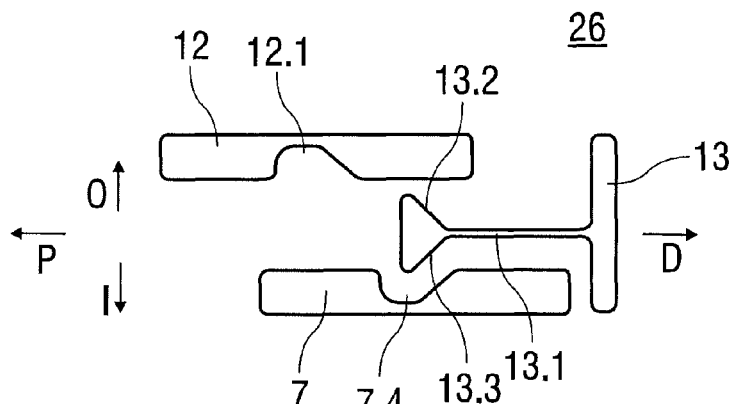
Figure 15C:
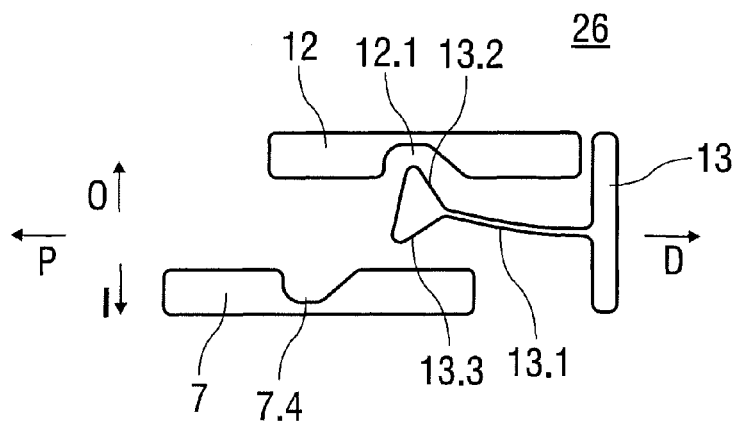

Note: the feedback component 28 is not illustrated in FIGS. 15A, 15B and 15C for clarity since it does not affect the function of the button release mechanism 26. A feedback release mechanism 31 for releasing the feedback component 28 is schematically illustrated in FIGS. 13A, 13B and 13C. Referring now to FIG. 13A, the feedback release mechanism 31 comprises the second resilient arms 30. A ramped inward boss 30.1 is arranged on each second resilient arm 30 which is engaged to a respective outward eleventh ramp 28.3 on the elongate portion 28.1 of the feedback component 28 in such a manner that the second resilient arm 30 is deflected in the outward direction O under load of the feedback spring 29. In an initial state A of the feedback release mechanism 31 the second resilient arms 30 are prevented from being outwardly deflected by outward support of the carrier 7 thus preventing translation of the feedback component 28 relative to the plunger 9. Hence, the feedback component 28 moves with the plunger 9 and remains in state A until immediately prior to fully expelling the medicament with the stopper 6 having almost bottomed out in the syringe 3 as illustrated in FIGS. 6A and 6B. At this point the plunger 9 has been translated in the proximal direction P relative to the carrier 7 to such an extent that the second resilient arms 30 reach an aperture 7.22 in the carrier 7 so the are no longer outwardly supported by the carrier 7. The feedback release mechanism 31 has thus arrived in a state B illustrated in FIG. 13B. Due to the ramped engagement between the ramped inward boss 30.1 and the outward eleventh ramp 28.3 the second resilient arm 30 is outwardly deflected under load of the feedback spring 29 thus disengaging the feedback component 28 from the plunger 9 and allowing the feedback component 28 to move in the distal direction D driven by the feedback spring 29 in a state C illustrated in FIG. 13C. Hence, the feedback component 28 is accelerated in the distal direction D and the distal end portion 28.2 impacts on the proximal extension 14.1 of the peg 14 on the trigger button 13 producing audible and tactile feedback to the user that medicament delivery is about finished (cf. FIGS. 7A and 7B).

FIGS. 7A and 7B show the auto-injector 1 with the stopper 6 having entirely bottomed out in the syringe 3.

As mentioned above the user is able to let the case 12 move by a few millimetres in the distal direction D under the force of the control spring 19 without affecting the position of the needle 4 as long as that motion is below a predefined distance. If the user wishes to end the injection, at any time, they must allow the case 12 to move in the distal direction D beyond that distance. FIGS. 8A and 8B show the auto-injector 1 with the chassis extended, e.g. when lifted from the injection site with the case 12 moved all the way in the distal direction D so that the chassis 2 protrudes from the proximal end of the case 12. As the case 12 is moved the first collar 20 releases the carrier 7 and then the second collar 21 releases from the case 12 and pulls the carrier 7 in the distal direction D. The sequencing of this switching is critical as retraction will fail if both collars 20, 21 are attached to the carrier 7 at the same time. This is overcome by separating the switching of the collars 20, 21 by a significant displacement of the case 12.

Figure 11E:
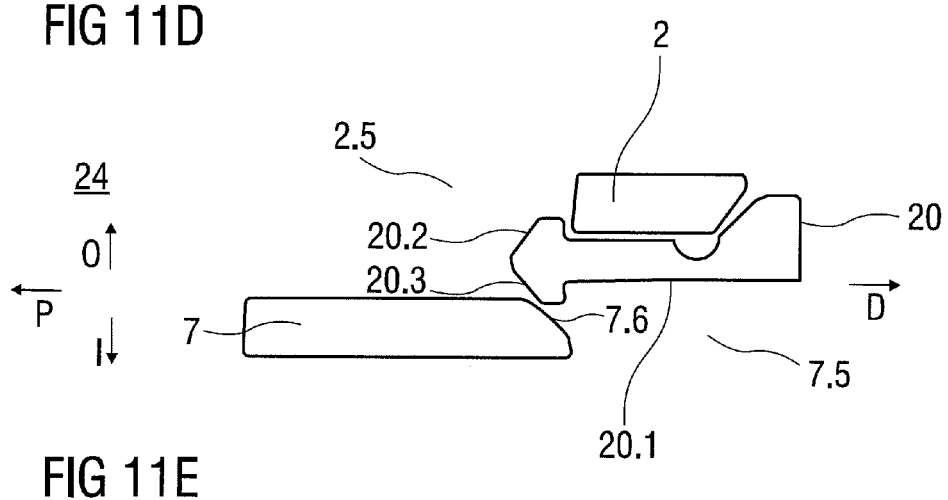
Figure 11F:
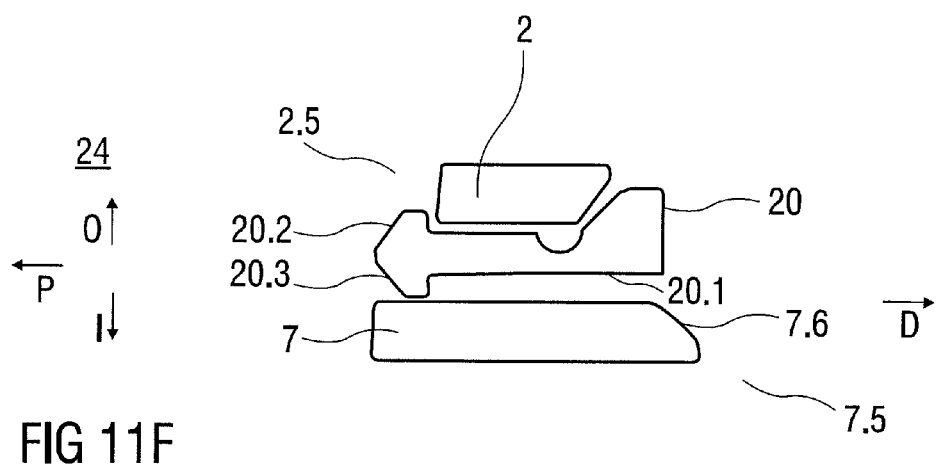

The switching of the first collar 20 is illustrated in FIGS. 11E and 11F. In FIG. 11E the case 12 has been allowed to move in the distal direction D under load of the control spring 19, e.g. during removal of the auto-injector 1 from the injection site. The first rib 12.3 (not illustrated, see FIG. 8A) is removed from outwardly behind the arrowhead 20.1. The first collar 20 is still being pushed in the proximal direction P by the control spring 19. Due to the engagement of the inward ninth ramp 20.3 on the arrowhead 20.1 with the distal tenth ramp 7.6 on the carrier 7 the arrowhead 20.1 is deflected in the outward direction O into the aperture 2.5 of the chassis 2 (illustrated in FIGS. 11A to 11F), the needle extension control mechanism 24 arriving in a state E as illustrated in FIG. 11E, decoupling the first collar 20 from the carrier 7 and latching it to the chassis 2.

Figure 12B:
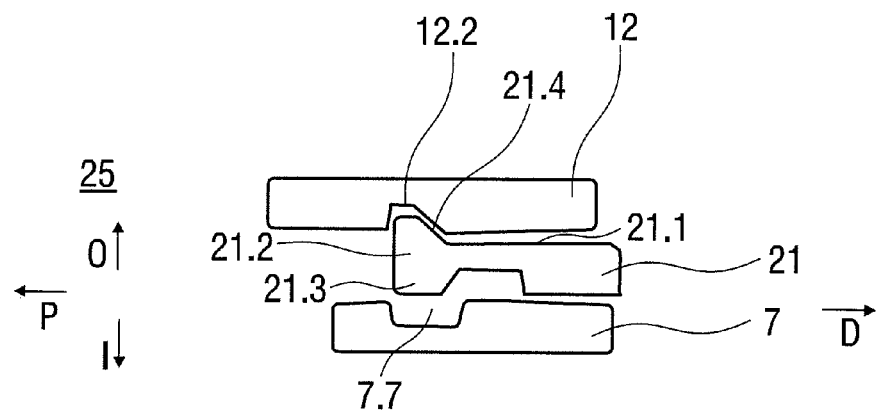
Figure 12C:
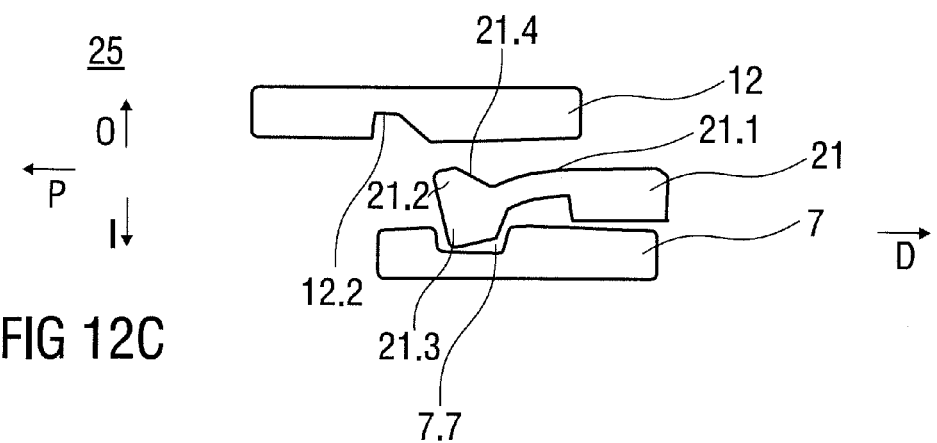

As the case 12 is moving further in the distal direction D relative to the chassis, e.g. on removal from the injection site, the syringe retraction control mechanism 25 switches from its state A (cf. FIG. 12A) into a state B illustrated in FIG. 12B. The case 12 and the second collar 21 locked to the case 12 move together in the distal direction D while the carrier 7 is held in place by the detent mechanism 18 in its state C as described above (cf. FIG. 10C). Due to this motion the inward boss 21.3 on the second beam head 21.2 of the proximal beam 21.1 on the second collar 21 no longer inwardly abuts the carrier 7. Instead the inward boss 21.3 is deflected in the inward direction I into a third recess 7.7 in the carrier 7 due to the ramped engagement of the second beam head 21.1 to the ramped second case detent 12.2 under load of the control spring 19. The syringe retraction control mechanism 25 thus arrives in a state C as illustrated in FIG. 12C with the second collar 21 decoupled from the case 12 and coupled to the carrier 7. The detent mechanism 18 applies a small retarding force to the movement of the carrier 7 before the syringe retraction control mechanism 25 switches to state C as there is a small sliding force, applied by the second collar 21, pulling the carrier 7 in the distal direction D on translation of the case 12 in the distal direction D when the needle extension control mechanism 24 has already been switched into state E. If the carrier 7 moves too far in the distal direction D before the second collar 21 switches, the case 12 runs out of travel before the inward boss 21.3 can deflect into the third recess 7.7 preventing retraction.

Starting from the position C of the detent mechanism 18 (cf. FIG. 10C) the carrier 7 and hence the rhomboid ramp member 7.1 are translated in the distal direction D under load of the control spring 19. Hence, the distal fifth ramp 7.3 of the rhomboid ramp member 7.1 engages the proximal third ramp 2.3 on the first beam head 2.2 of the resilient beam 2.1 in a manner deflecting the resilient beam 2.1 in the inward direction I. This applies the small retarding force to the movement of the carrier 7 required for ensuring the switching of the second collar 21 to the carrier 7. The resilient beam 2.1 and the rhomboid ramp member 7.1 are offset sideways to allow the resilient beam 2.1 to pass without contacting the rhomboid ramp member 7.1 as soon as the first beam head 2.2 is entirely inwardly from the ramp member 7.1 in a state D illustrated in FIG. 10D.

Figure 10D:
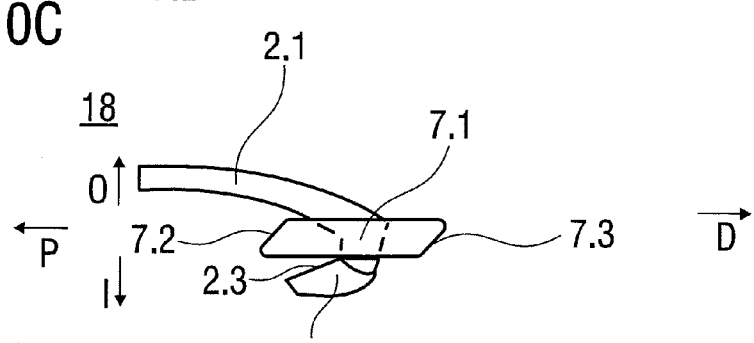

The control spring 19 is grounded at its proximal end in the case by the first collar 20 being abutted against the chassis 2. The distal end of the control spring 19 moves the second collar 21 in the distal direction D taking with it the carrier 7 and hence the syringe 3 with the needle 4 overcoming the detent mechanism 18 as illustrated in FIG. 10D. Note that the needle 4 is retracted by the auto-injector 1 as soon as the user allows the case 12 to translate sufficiently far as opposed to auto-injectors with needle shields which require the user to remove the auto-injector from the injection site thereby themselves pulling the needle out of the skin for allowing the needle shield to advance.

Note that prior to refraction, the space between the rib on the plunger 9 and the distal end portion 28.2 of the feedback component 28, where the feedback spring 29 is grounded is greater than the free length of the feedback spring 29. This means as the carrier 7 retracts (i.e. reducing the distance between the plunger 9 and the feedback component 28) the feedback spring 29 does not require recompression and thus does not provide any retarding force.

To prevent the feedback component 28 rattling at the end of dose and prior to retraction, it may be considered to make the free length of the feedback spring 29 equal to the space between the rib on the plunger 9 and the distal end portion 28.2 of the feedback component 28. In this case, during retraction, the feedback spring 29 would require recompression, reducing the force driving the final part of retraction. Nevertheless, the feedback spring 29 is very low rate and has been calculated to be within acceptable tolerance limits for reliable retraction.

The retraction ends when the distal collar 21 meets a first back stop 12.4 on the case 12 as in FIGS. 9A and 9B. The arrowhead 20.1 on the first collar 20 is inwardly supported by the carrier 7 in a state F illustrated in FIG. 11F and thus prevented from deflecting in the inward direction I. The outward sixth ramp 20.2 of the arrowhead 20.1 is engaged behind the first rib 12.3 on the case 12 preventing the case 12 from being pushed in the proximal direction P again. A clearance may be provided between the arrowhead 20.1 and the first rib 12.3 to allow for tolerances.

The detent mechanism 18 returns to state A as in FIG. 10A locking the carrier 7 in position relative to the chassis 2 as it did initially, however it cannot be unlocked now as the case 12 cannot move relative to the chassis 2.

A tab 20.4 on the first collar 20 is now visible through an indicator window 32 in the case 12—indicating the auto-injector 1 has been used.

Figure 16:
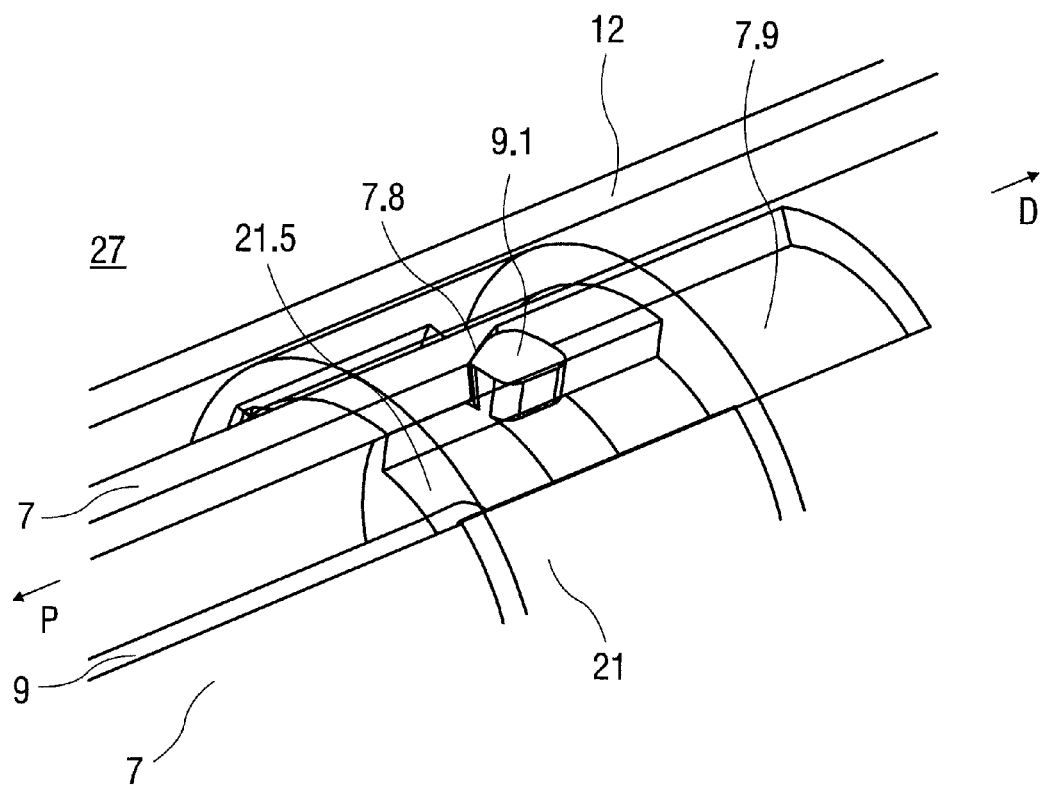
FIG. 16 is an isometric view of an alternative embodiment of the plunger release mechanism.

FIG. 16 is an isometric view of an alternative embodiment of the plunger release mechanism 27. The plunger release mechanism 27 prevents movement of the plunger 9 in the proximal direction P relative to the carrier 7 until the carrier 7 is moved in the proximal direction P for needle extension. As opposed to the plunger release mechanism 27 of FIG. 14, where relative movement of the carrier 7 and trigger button 13 are used to trigger the release of the plunger 9, the alternative embodiment of FIG. 16 releases the plunger 9 by movement of the carrier 7 relative to the second collar 21. FIG. 16 illustrates the plunger release mechanism 27 prior to plunger release. The second collar 21 is shown transparent to improve clarity. The plunger 9 is being pushed in the proximal direction P by the drive spring 8. In order for the plunger 9 to advance, it must rotate around a twelfth ramp 7.8 on the carrier 7. A ramp member 9.1 on the plunger 9 is arranged to engage this twelfth ramp 7.8. Rotation of the ramp member 9.1 is blocked by an inward longitudinal rib 21.5 on the second collar 21 splined in a longitudinal aperture 7.9 in the carrier 7. The case 12 and the second collar 21 remain in the same position, i.e. coupled to each other for joint axial translation. On depression of the trigger button 13 the carrier 13 and the plunger 9 being part of the drive sub-assembly are moved in the proximal direction P, first by the user pressing the trigger button 13 and then by the control spring 19 taking over via the first collar 20 as described above. Once the carrier 7 moves sufficiently far in the proximal direction P relative to the second collar 21 the ramp member 9.1 on the collar 9 comes clear of the longitudinal rib 21.5 on the second collar 21 and can rotate past the proximal end of the longitudinal rib 21.5 due to its ramped engagement to the twelfth ramp 7.8 under load of the drive spring 8. Hence, the drive spring 8 advances the plunger 9 in the proximal direction P for expelling the medicament M.

Figure 17:
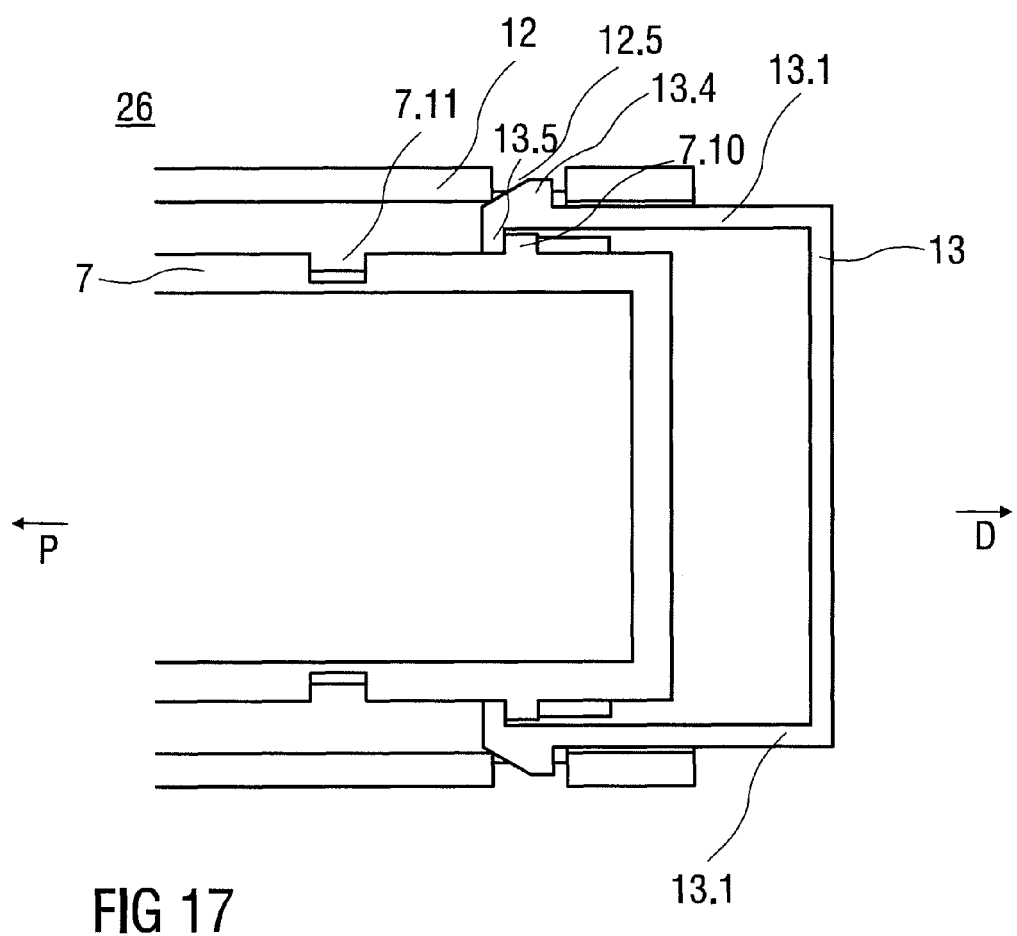
FIG. 17 is a longitudinal section of an alternative embodiment of the button release mechanism.

FIG. 17 is a longitudinal section of an alternative embodiment of the button release mechanism 26. Other than the button release mechanism 26 of FIG. 15 which gives the appearance of a revealing trigger button 13 on skin contact by switching the ground of the trigger button 13 between the carrier 7 and the case 12, the button release mechanism 26 of FIG. 17 starts with the trigger button 13 locked but protruding from the distal end of the case 12. Once the carrier 7 has moved in the distal direction D on skin contact of the chassis 2, it is possible to depress the trigger button 13 and activate the auto-injector 1. This ensures a sequenced operation.

In the embodiment of FIG. 17 the trigger button 13 has two proximal beams 13.1, each of them having a ramped outward boss 13.4. In the initial state shown in FIG. 17 the ramped outward bosses 13.4 are engaged in respective fourth recesses 12.5 in the case 12. Disengaging the ramped outward bosses 13.4 from the fourth recesses 12.5 is prevented by the carrier 7 inwardly supporting the proximal beams 13.1 in a manner to keep the proximal beams 13.1 from deflecting inwardly. Inward protrusions 13.5 on the proximal beams 13.1 abut against a second rib 7.10 on the carrier 7 in a manner preventing the carrier 7 from moving further in the proximal direction P in the initial state. Once the carrier 7 has moved in the distal direction D on skin contact of the chassis 2 a first window 7.11 in the carrier 7 is moved behind the inward protrusion 13.5 so as to allow the proximal beams 13.1 to be inwardly deflected due to their ramped engagement in the fourth recesses 12.5 on depression of the trigger button 13. The proximal beams 13.1 are now outwardly supported by the case 12 and remain engaged to the carrier 7 even on retraction of the needle 4. The trigger button 13 does therefore not return to its initial position, indicating that the auto-injector 1 has been used.

Figure 18A:
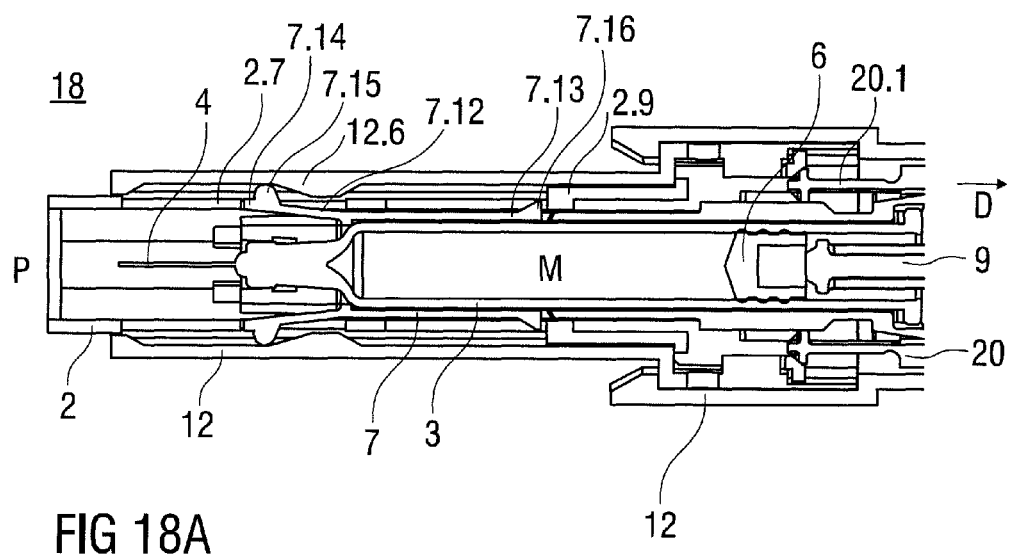
FIG. 18 shows longitudinal sections of an alternative embodiment of the detent mechanism.
Figure 18B:
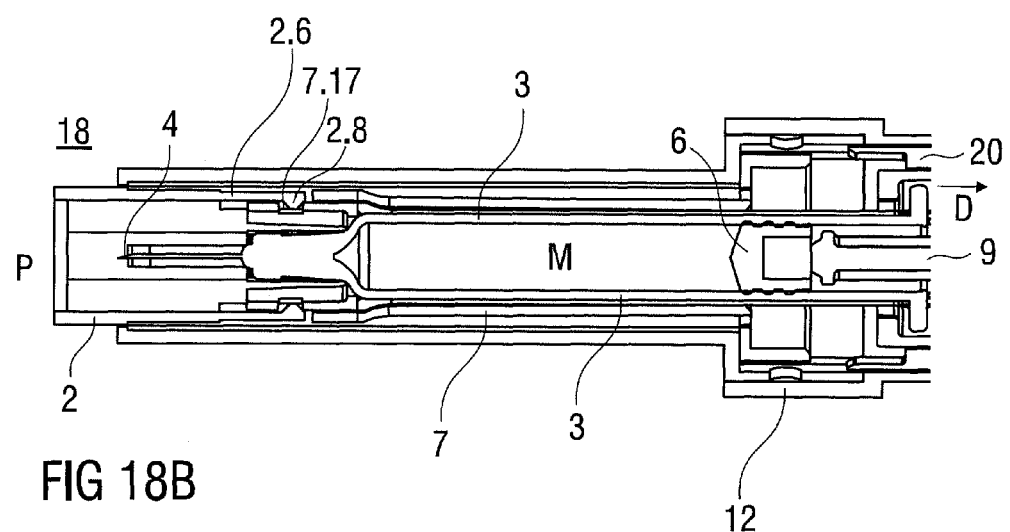

FIGS. 18A and 18B show two longitudinal sections of an alternative embodiment of the detent mechanism 18. The detent mechanism 18 of FIGS. 10A to 10D, which may be referred to as a "race track" mechanism because of the first beam head 2.2 travelling around the rhomboid ramp member 7.1 has multiple functions which control the movement of the carrier 7 relative to the chassis 2. The alternative detent mechanism 18 of FIGS. 18A and 18B uses three clips 7.12, 7.13, 2.6 to produce the same effect.

The first clip 7.12 is arranged as an outwardly biased resilient beam on the carrier 7 extending from the carrier 7 in the proximal direction P. the first clip 7.12 is arranged to prevent the carrier 7 from being moved in the proximal direction P prior to the chassis 2 being depressed or rather the case 12 being translated on skin contact. The first clip 7.12 is composed of two sections side by side. A first section 7.14 prevents movement of the carrier 7 in the proximal direction P by abutting the chassis 2 in a recess. A second section 7.15 is arranged as an outwardly protruding clip head arranged to be ramped inwards by a ramp feature 12.6 on the chassis 12 for releasing the first clip 7.12 thereby unlocking the carrier 7 from the chassis 2 when the case 12 is being translated in the proximal direction P on skin contact. A longitudinal slot 2.7 in the chassis 2 is arranged for allowing the second section 7.15 to slide in the proximal direction P once the lock has been released. A slight friction force between the first clip 7.12 and the chassis 2 provides the retarding force required to ensure retraction.

The second clip 7.13 is arranged as a resilient beam on the carrier 7 extending in the distal direction D having an outwardly protruding third beam head 7.16 with a proximal ramp. The third beam head 7.16 serves as a back stop against a third rib 2.9 on the chassis 2 for preventing the carrier 7 moving in the distal direction D from its initial position. The carrier 7 and chassis 2 are assembled with the second clip 7.13 in this position prior to inserting the syringe 3 into the carrier 7 which is facilitated by the proximal ramp on the third beam head 7.16. The syringe 3 locks the clip in place by preventing inward deflection thus creating a fixed stop.

The third clip 2.6 is a resilient beam on the chassis 2 extending in the distal direction D. A ramped fourth beam head 2.8 on the third clip 2.6 is arranged to inwardly engage in a fifth recess 7.17 in the carrier 7. Once the first clip 7.12 is unlocked, the user can load the third clip 2.6 by pressing the carrier 7 in the proximal direction P on depression of the trigger button 13. The third clip 2.6 is loaded in compression, i.e. it will bend outwards and release suddenly due to its ramped engagement to the carrier 7 providing the detent functionality similar to that illustrated in FIG. 10B.

Figure 19:
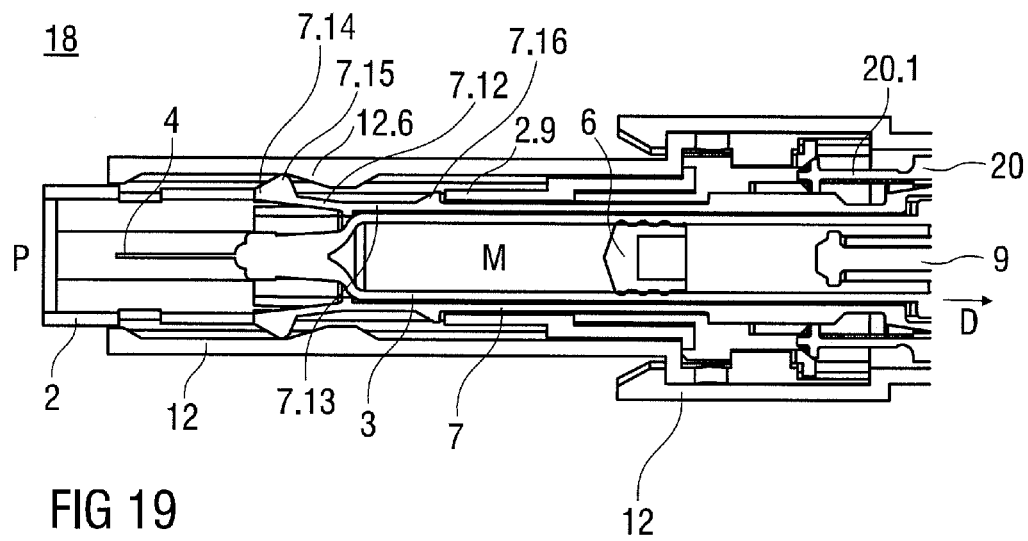
FIG. 19 is a longitudinal section of a third embodiment of the detent mechanism.

FIG. 19 is a longitudinal section of a third embodiment of the detent mechanism 18 which is a variation on the embodiment of FIGS. 18A and 18B. In this embodiment the detent function of the third clip 2.6 has been added into the first clip 7.12. The lock between the case 12 and the carrier 7 is released in the same way, but the detent is provided by deflecting the first clip 7.12 inwards a second level which is achieved by the chassis 2 not having a slot 2.7 for the second section 7.15. Instead the second section 7.15, once ramped inwards by the ramp feature 12.6 on the case 12 has to be further ramped inwards inside the chassis 2 on axial load between the chassis 2 and the carrier 7, suddenly releasing their engagement.

Figure 20:
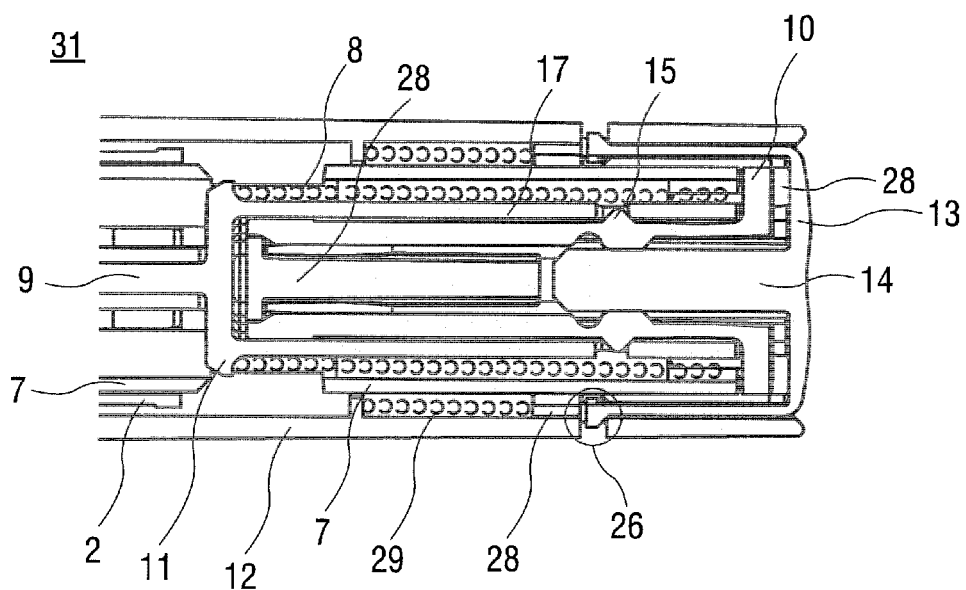
FIG. 20 is a longitudinal section of an alternative embodiment of the feedback release mechanism.

FIG. 20 is a longitudinal section of an alternative embodiment of the feedback release mechanism 31. As opposed to the feedback release mechanism 31 of FIG. 13 where the feedback spring 29 acts between the plunger 9 and the feedback component 28, in the embodiment illustrated in FIG. 20 the feedback spring 29 acts between the case 12 and the feedback component 28. During needle extension the feedback spring 29 is compressed as the feedback component 28 moves with the carrier 7 relative to the case 12. When the feedback component 28 is released by the plunger 9 shortly before the end of dose, the feedback component 28 moves in the distal direction D and impacts the trigger button 13. Other than in FIG. 13 the feedback spring 29 is not being recompressed during needle retraction since it is grounded in the case 12 not in the plunger 9.

Figure 21A:
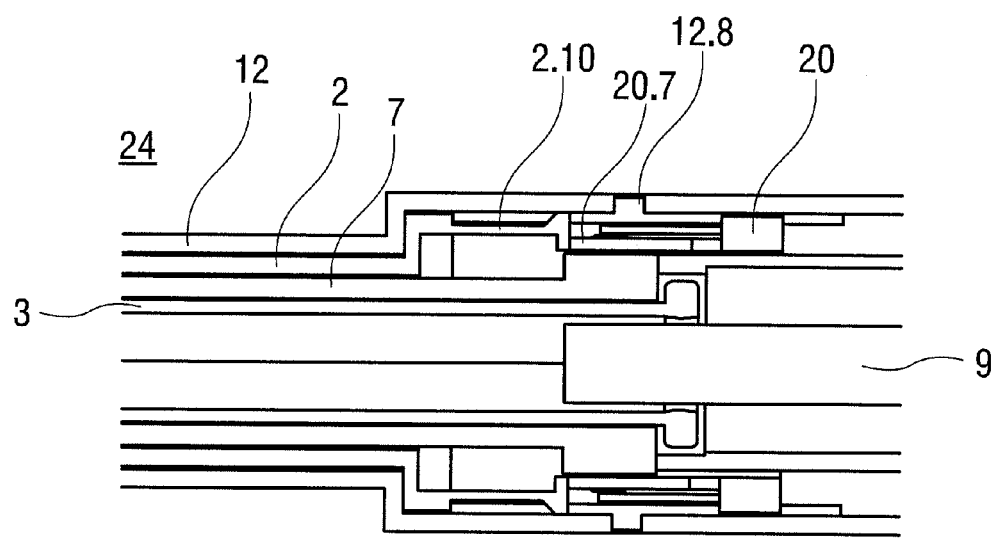
FIG. 21 shows longitudinal sections of an alternative embodiment of the needle extension control mechanism, also arranged to perform the function of the detent mechanism on needle retraction and needle extension.
Figure 21B:
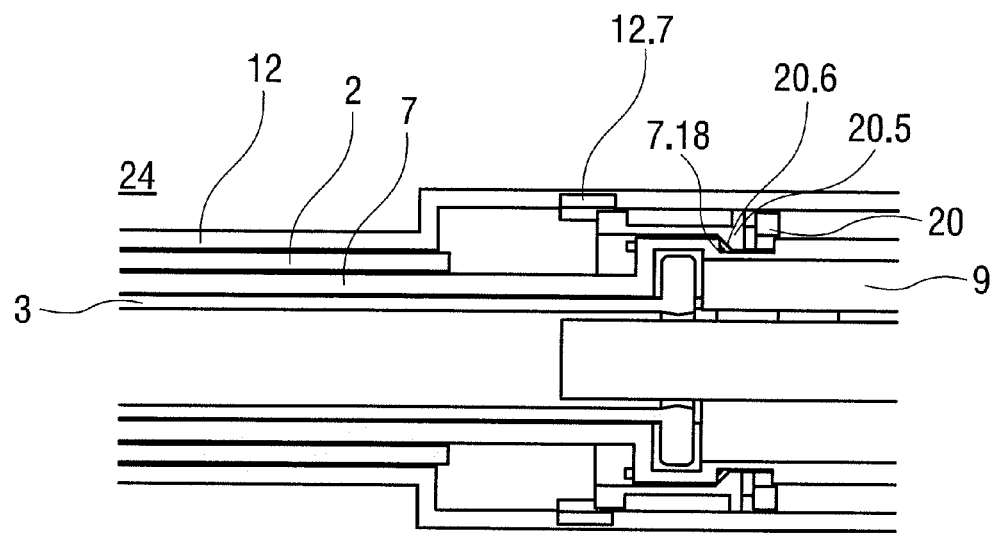
Figure 22:
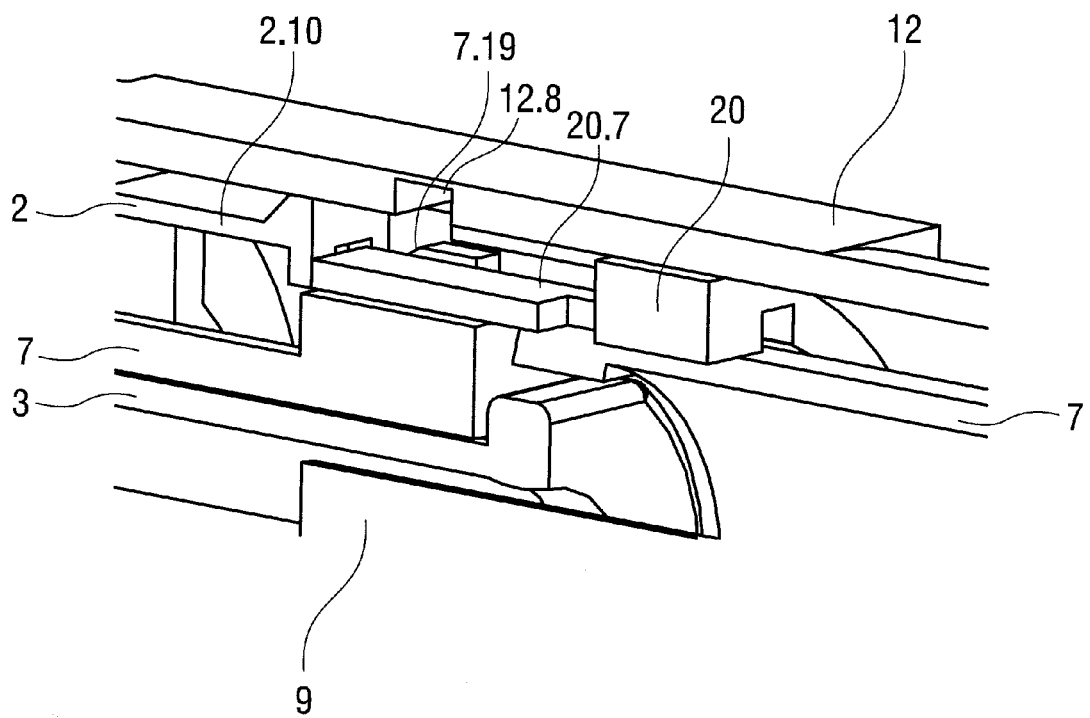
FIG. 22 is an isometric view of the needle extension control mechanism of FIG. 21.

FIGS. 21A and 21B show longitudinal sections of an alternative embodiment of the needle extension control mechanism 24 which is also arranged to perform the detent function of the detent mechanism 18 on needle retraction and needle extension. FIG. 22 shows a corresponding isometric view. A fourth clip 20.5 on the first collar 20 is arranged as a resilient beam with a beam head having an inward proximal thirteenth ramp 20.6 for engaging a fourth rib 7.18 on the carrier 7 and outwardly supported by the case 12 so as to keep the first collar 20 engaged to the carrier 7 prior to use, during needle extension and during expelling the medicament. When the case 12 moves in distal direction relative to the carrier, e.g. when the user lifts the case 12 away from the injection site at the end of injection, a sixth recess 12.7 in the case 12 is moved outwardly behind the fourth clip 20.5 allowing the fourth clip 20.5 to release when the carrier 7 is pulled in the distal direction D by the second collar 21. Since the fourth clip 20.5 has to be ramped outwards a small force is required to release the fourth clip 20.5, providing the retraction detent.

A fifth clip 2.10 on the chassis 2 abuts a block 20.7 on the first collar 20 prior to use preventing the first collar 20 and hence the carrier 7 engaged to the first collar 20 from moving in the proximal direction P. In order to release, the fifth clip 2.10 must be deflected outwards and over the block 20.7. Outward deflection of the fifth clip 2.10 is initially prevented by the case 12. Once the case 12 has moved on skin contact a second window 12.8 in the case 12 appears outwardly from the fifth clip 2.10 allowing outward deflection. The fifth clip 2.10 is then deflected by a fourteenth ramp 7.19 on the carrier 7 when the carrier 7 is pushed in the proximal direction P on button depression as the fourth clip 20.5 does allow translation of the carrier 7 in the proximal direction P relative to the first collar 20 but not the other way round. The detent for needle extension is provided by having to deflect the fifth clip 2.10 when it is loaded by the control spring 19.

Figure 23A:
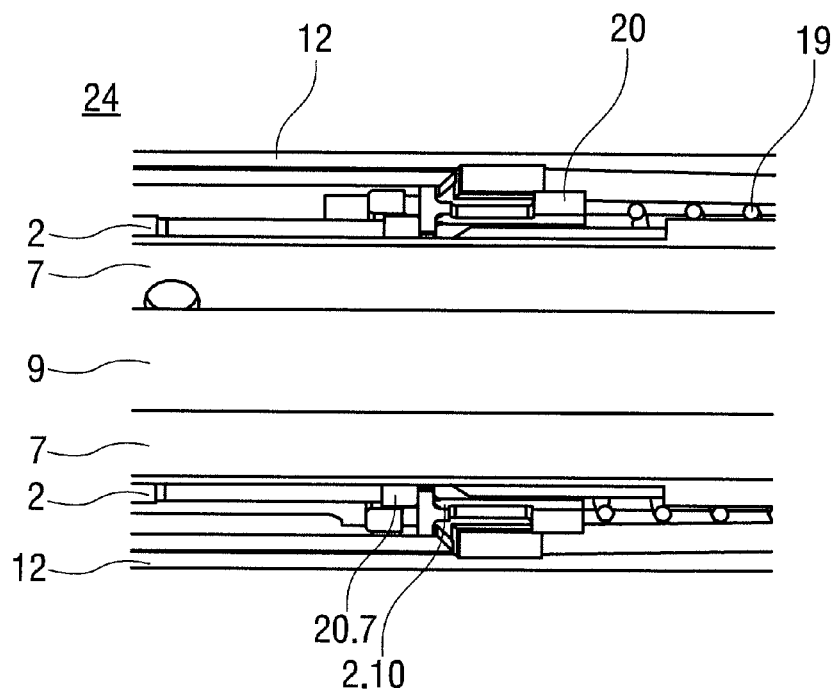
FIG. 23 shows longitudinal sections of a third embodiment of the needle extension control mechanism, also arranged to perform the functions of the detent mechanism.
Figure 23B:
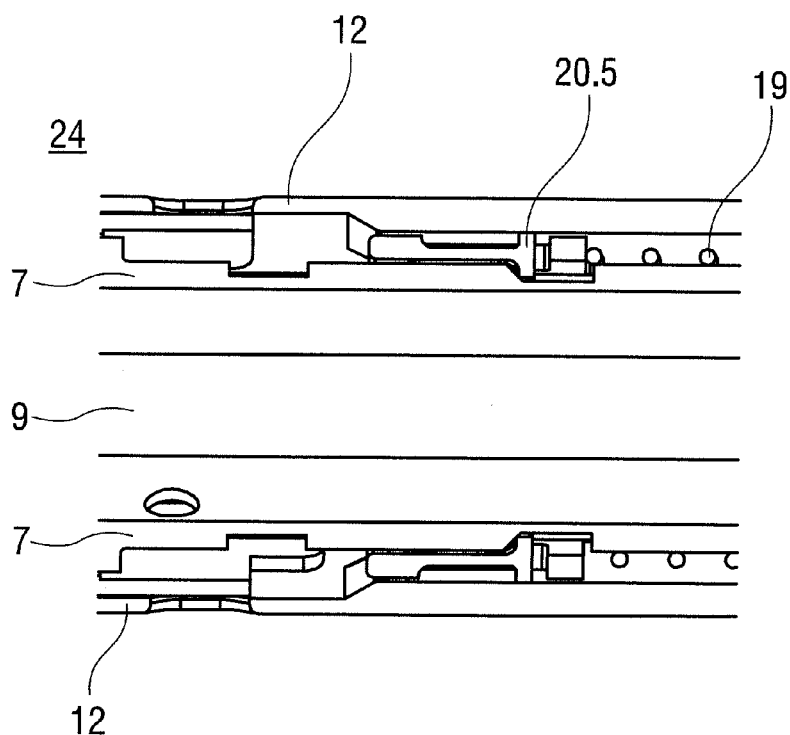
Figure 24:
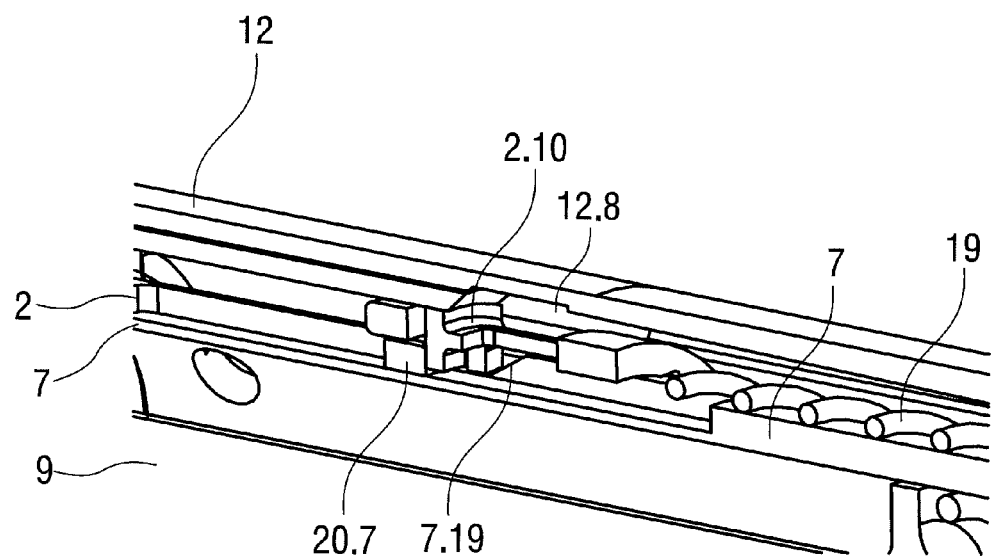
FIG. 24 is an isometric view of the needle extension control mechanism of FIG. 23.

FIGS. 23A and 23B show longitudinal sections of a third embodiment of the needle extension control mechanism 24, also arranged to perform the functions of the detent mechanism 18. FIG. 24 is an isometric view of the needle extension control mechanism 24 of FIG. 23. The embodiment is similar to that illustrated in FIGS. 21A, 21B and 22. The difference is that the fifth clip 2.10 is arranged on the first collar 20 and the block 20.7 is arranged on the chassis 2, i.e. their position has been switched, so there are two clips 2.10 and 20.5 on the first collar 20.

The fourth clip 20.5 is identical to that in FIG. 21B. It keeps the first collar 20 connected to the carrier 7 until the needle retraction is triggered, ensuring full needle extension length or depth is reached and maintained until the retraction cycle is initiated by displacing the case backwards in distal direction relative to the chassis, e.g. when removing the auto-injector 1 from the skin.

The fifth clip 2.10 provides the detent for needle extension and releases the first collar 20 from the chassis 2, initiating needle extension. The fifth clip 2.10 prevents the first collar 20 and hence the carrier 7 engaged to the first collar 20 from moving in the proximal direction P prior to use by abutting the block 20.7 on the chassis 2. In order to release, the fifth clip 2.10 must be deflected outwards and over the block 20.7. Outward deflection of the fifth clip 2.10 is initially prevented by the case 12. Once the case 12 has moved on skin contact the second window 12.8 in the case 12 appears outwardly from the fifth clip 2.10 allowing outward deflection. The fifth clip 2.10 is then deflected by the fourteenth ramp 7.19 on the carrier 7 when the carrier 7 is pushed in the proximal direction P on button depression as the fourth clip 20.5 does allow translation of the carrier 7 in the proximal direction P relative to the first collar 20 but not the other way round. The detent for needle extension is provided by having to deflect the fifth clip 2.10 when it is loaded by the control spring 19.

Figure 25A:
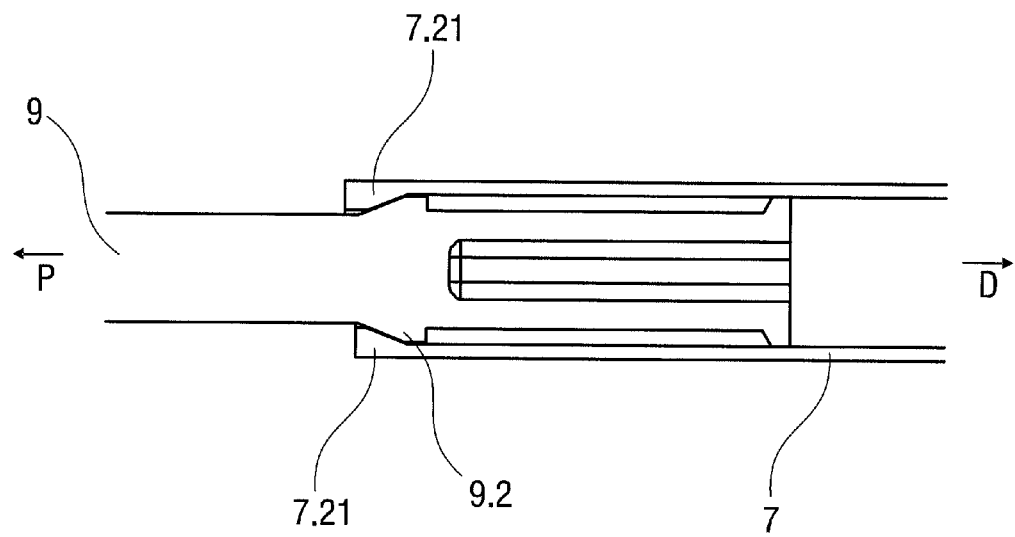
FIG. 25 shows longitudinal sections of a third embodiment of the feedback release mechanism.
Figure 25B:
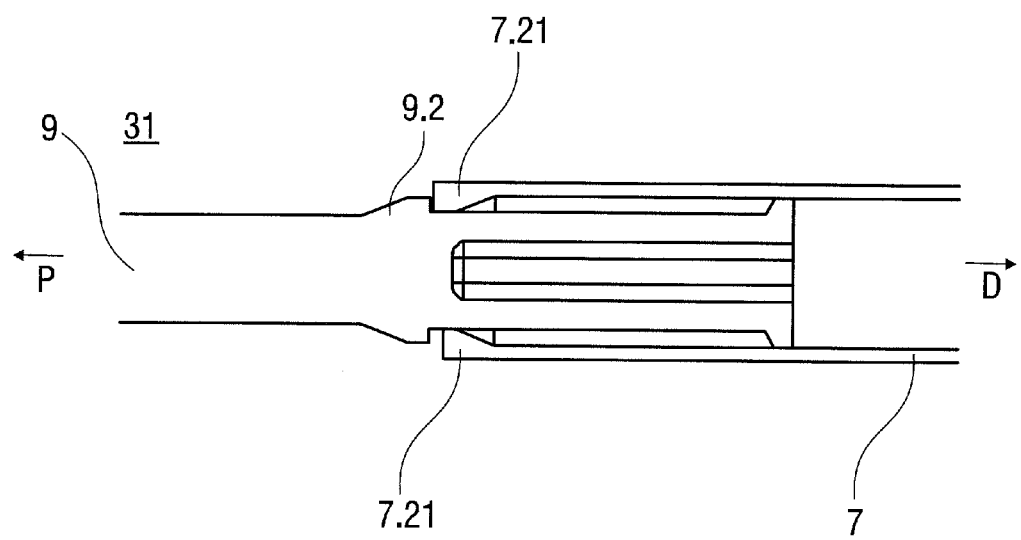

FIGS. 25A and 25B show a longitudinal section of a third embodiment of the feedback release mechanism 31. This embodiment works without the need for a dedicated feedback spring. The plunger 9 comprises a proximally ramped rib 9.2 arranged to splay two seventh clips 7.21 on the carrier 7 immediately prior to the end of dose. When the proximally ramped rib 9.2 has travelled past the seventh clips 7.21 they snap back and impact the plunger 9 generating a sound. The tubular shape of the carrier 7 helps to transmit the sound. FIG. 25A shows the feedback release mechanism 31 before release. FIG. 25B shows the feedback release mechanism 31 after release. Proximal faces of the seventh clips 7.21 on the carrier 7 are axially offset to facilitate assembly by lifting the seventh clips 7.21 over the distal side of the proximally ramped rib 9.2 one by one.

Figure 26A:
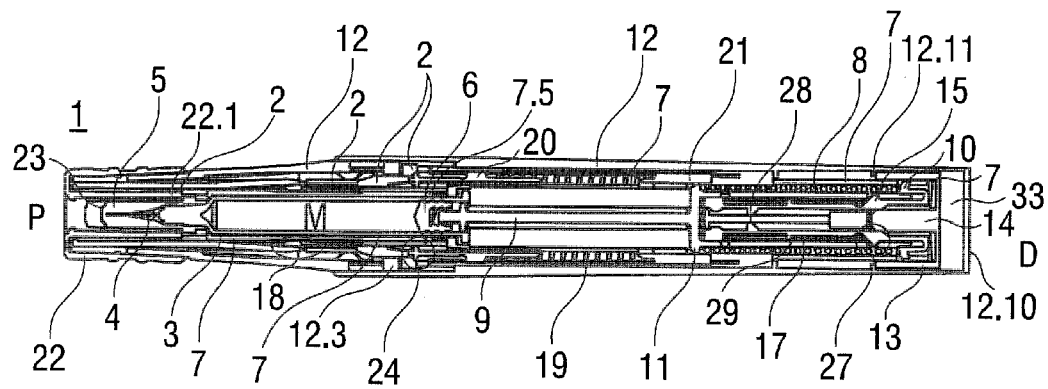
FIG. 26 is another embodiment of the auto-injector having a wrap-over sleeve trigger instead of a trigger button.
Figure 26B:
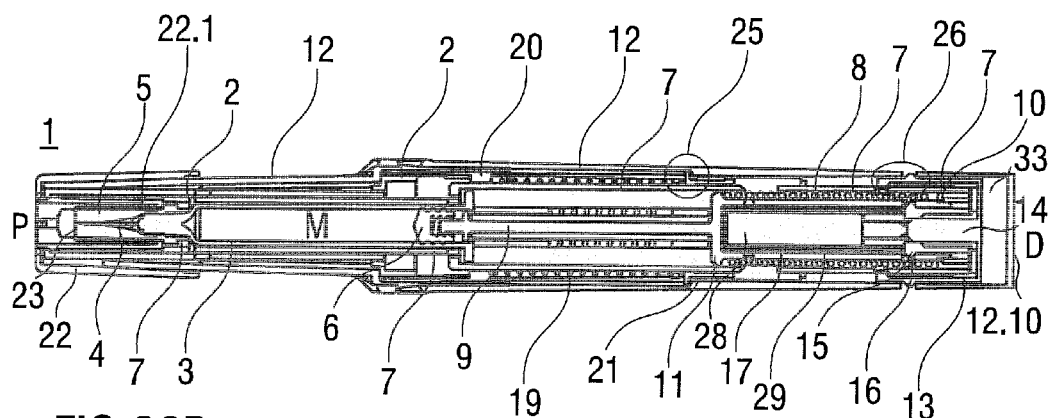

FIGS. 26A and 26B show longitudinal sections of another embodiment of the auto-injector 1 in different section planes, the different section planes approximately 90° rotated to each other, wherein the auto-injector 1 is in an initial state prior to use. The auto-injector 1 is essentially identical to the one described in FIGS. 1 to 15. However, other than the auto-injector of FIGS. 1 to 15 the auto-injector 1 of this embodiment has a wrap-over sleeve trigger instead of a trigger button.

The wrap-over sleeve trigger 12 is the same component as the case 12 which has a closed distal end face 12.10 other than the one in FIGS. 1 to 15. An internal trigger button 13 is arranged at the distal end inside the sleeve trigger 12. Other than in FIGS. 1 to 15 the trigger button 13 is not visible nor does it protrude from the case 12 in any state. In the initial state a clearance 33 is provided between the distal end face 12.10 of the sleeve trigger 12 and the internal trigger button 13 allowing for some travel of the sleeve trigger 12 without interfering with the trigger button 13.

As the auto-injector 1 does not differ from the auto-injector of FIGS. 1 to 15 in other respects it is essentially operated in the same way with the following exceptions:

As the chassis 2 is placed against the injection site the sleeve trigger 12 translates in the proximal direction P relative to the chassis 2 into the advanced position in a first phase of sleeve travel removing the clearance 33 between the distal end face 12.10 of the sleeve trigger 12 and the internal trigger button 13. As in the embodiment of FIGS. 1 to 15 this motion unlocks the detent mechanism 18 and the trigger button 13. As the user continues to depress the sleeve trigger 12 in a second phase of sleeve travel thereby further advancing it in the proximal direction P the distal end face 12.10 hits the internal trigger button 13 thereby depressing it until the first collar 20 is released from the chassis 2 and the control spring force is coupled on to the carrier 7. The carrier 7 then advances until the internal trigger button 13 stops on another rib in the case 12 and the plunger release mechanism 27 is released (note the peg 14 is shorter in this embodiment.

From a user perspective, the detent mechanism 18 is arranged to provide a resistive force when the user reaches the second phase of sleeve travel. Internally, there is no difference to the embodiment of FIGS. 1 to 15 at this point.

Needle extension is triggered by the user fully advancing the sleeve trigger 12 in the second phase of sleeve travel thereby fully depressing the internal trigger button 13 and overcoming the detent mechanism as in the embodiment of FIGS. 1 to 15.

As the control spring 19 takes over on button depression fully advancing the carrier 7 for needle extension the internal trigger button 13 bottoms out on an internal fifth rib 12.11 in the sleeve trigger 12 and the internal trigger button 13 switches back to being locked to the sleeve trigger 12 as in a third state shown in FIG. 15C.

The embodiment of FIGS. 26A and 26B may also be combined with the alternative features illustrated in FIGS. 16 to 25.

Figure 27:
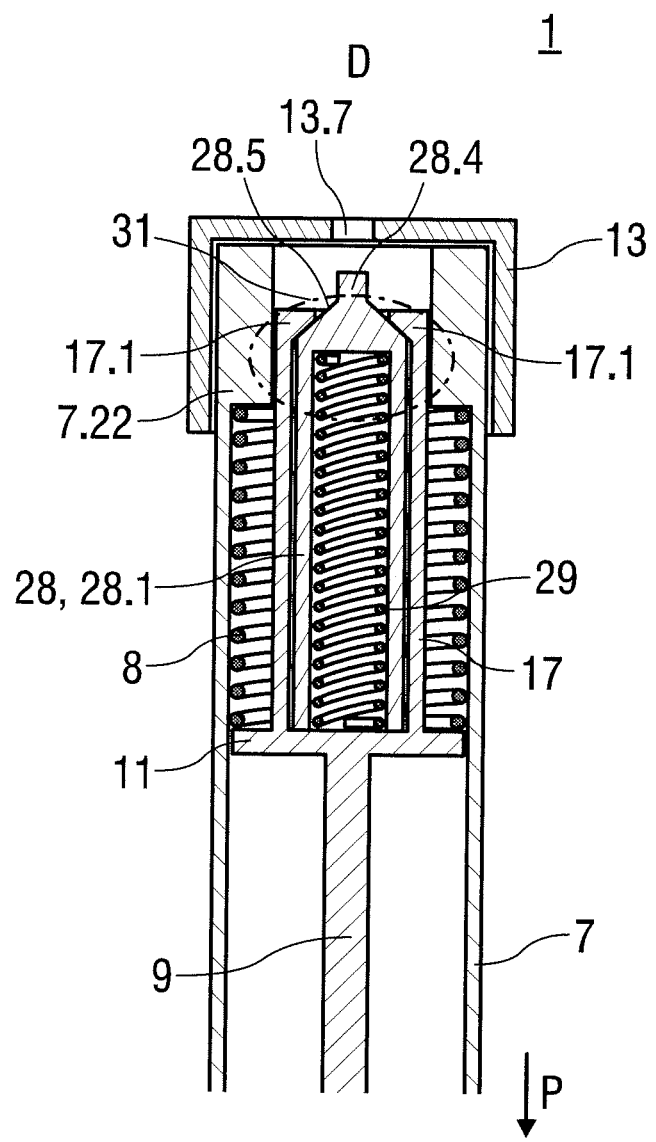
FIG. 27 is a longitudinal section of the distal end of an auto-injector with an alternative feedback release mechanism prior to actuation.

FIG. 27 is a longitudinal section of the distal end of an auto-injector 1 with an alternative feedback release mechanism 31 prior to actuation in a first position. A plunger 9 for acting on a syringe or stopper (not illustrated) is retained within a syringe carrier 7. A trigger button 13 is arranged over the distal end of the syringe carrier 7. A drive spring 8 is arranged within the carrier 7, distally grounded in the carrier 7 and proximally bearing against a thrust face 11 on the plunger 9. A distal plunger sleeve 17 is attached distally to the thrust face 11 and arranged inside the drive spring 8. A feedback component 28 comprises an elongate portion 28.1 arranged within the distal plunger sleeve 17 and a distal end pin 28.4 which is entirely situated within the carrier 7 in the first position and can therefore not be seen or felt by a user.

A feedback spring 29 is arranged to bias the feedback component 28 in the distal direction D relative to the plunger 9 by proximally bearing against the thrust face 11 and distally against the feedback component 28.

Both, the drive spring 8 and the feedback spring 29 are pre-stressed. The plunger 9 is engaged to the carrier 7 by a plunger release mechanism (not illustrated). The plunger release mechanism may be arranged as in one of the above described embodiments.

The distal plunger sleeve 17 comprises two resilient ramped latches 17.1 retaining the feedback component 28 by engaging a ramped surface 28.5 thereof. The latches 17.1 are outwardly supported by a thickened wall portion 7.23 of the carrier 7 in a manner to prevent them from being outwardly deflected by ramp action under force from the feedback spring 29. Hence, the feedback component 28 cannot be released in this configuration.

Figure 28:
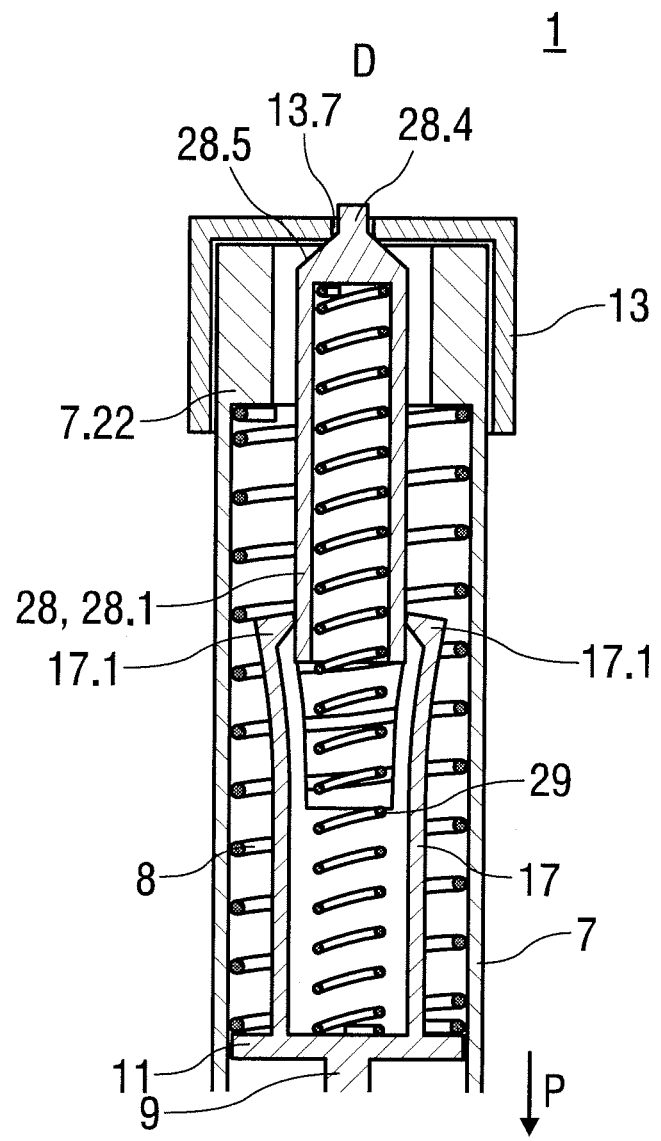
FIG. 28 is a longitudinal section of the distal end of the auto-injector with the alternative feedback release mechanism of FIG. 27 after release.

FIG. 28 is a longitudinal section of the distal end of the auto-injector 1 with the alternative feedback release mechanism 31 of FIG. 27 after release in a second position.

The plunger 9 has been released by the plunger release mechanism and hence translated in the proximal direction P for displacing the stopper. During the proximal movement of the plunger 9 the ramped latches 17.1 on the distal plunger sleeve 17 have left the thickened wall portion 7.23 and entered a widened portion allowing them to deflect outwardly due to ramped action under force from the feedback spring 29. The feedback component advances in the distal direction D driven by the feedback spring 29 through the distal end of the carrier 7 whereby the distal end pin 28.4 eventually protrudes from the distal end of the trigger button 13 through a bore 13.7 therein when the feedback component 28 reaches the second position. The distal end pin 28.4 can thus be seen by the user. In case the user still keeps their thumb pressed on the trigger button 13 they can also feel the distal end pin 28.4 with their thumb. Furthermore, the ramped surface 28.5 hitting the trigger button 13 from inside can generate both an audible feedback and a tactile impact.

The distal plunger sleeve 17 may have one or more resilient ramped latches 17.1. The at least one resilient ramped latch 17.1 may likewise be connected directly to the thrust face 11 on the plunger 9 so that the distal plunger sleeve 17 would not be required.

The trigger button 13 may be connected to the carrier 7 or to a case (not illustrated) surrounding the carrier 7. The trigger button 13 does not necessarily have to remain in the same longitudinal position with respect to the carrier 7. Instead, at the end of dose the trigger button 13 can still be positioned at the end of the case (not illustrated) while the carrier 7 with all its internal components has advanced within the case. For this purpose the feedback spring 29 and the feedback component 28 have to be designed accordingly strong and long to ensure that the feedback component 28 still reaches the trigger button 13 at the end of dose so that the distal end pin 28.4 can protrude from the trigger button 13.

The feedback component 28 may be designed to be released prior to the plunger 9 and stopper reaching their end of dose position, preferably shortly prior to this event.

The noise component 28 according to FIGS. 27 and 28 may be combined with the embodiments illustrated in FIGS. 1 to 26, wherein the respective trigger button 13 or wrap-over sleeve trigger 12 would be provided with the bore 13.7 and the feedback component 28 would have a distal end pin 28.4. The release of the feedback component 28 could be achieved either by the feedback release mechanism 31 of FIGS. 27 and 28 or by one of the feedback release mechanisms 31 illustrated in the other embodiments.

The noise release mechanism 31 according to FIGS. 27 and 28 may likewise be applied in other types of auto-injectors. For example, the syringe carrier 7 may be used as part of a case or housing instead of being arranged within an extra case. Likewise, the bore 13.7 may be arranged in a part of a case or a wrap-over sleeve trigger instead of the trigger button 13.

The distal end pin 28.4 may have a different colour than the trigger button 13, e.g. red in order to improve the visual indication making the user aware that the end of dose has been reached and that the device is used.

It goes without saying that in all ramped engagements between two components described in the above embodiments there may be just one ramp on one or the other component or there may be ramps on both components without significantly influencing the effect of the ramped engagement.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An injection device for administering a dose of a medicament, comprising:
   a case having a proximal end and a distal end;
   a carrier adapted to accommodate a syringe;
   and a trigger button,
   wherein, in a first state, the trigger button is coupled to the case or the carrier or both the case and the carrier and abuts the distal end of the case such that the trigger button cannot be depressed in a proximal direction,
   wherein, in an intermediate state following the first state, the case moves proximally relative to the carrier and the trigger button causing the trigger button to protrude from the distal end of the case, and the trigger button engages the carrier, and
   wherein, in a second state following the intermediate state, the trigger button and the carrier move proximally relative to the case and the trigger button disengages the carrier and engages the case.

2. The injection device according to claim 1, wherein the trigger button includes a deflectable beam adapted to engage the case and the carrier.

3. The injection device according to claim 2, wherein the case includes a case detent adapted to engage the beam.

4. The injection device according to claim 3, wherein the beam includes a first ramp adapted to engage the case detent.

5. The injection device according to claim 3, wherein the carrier includes a carrier detent adapted to engage the beam.

6. The injection device according to claim 5, wherein the beam includes a second ramp adapted to engage the carrier detent.

7. The injection device according to claim 6, wherein, in the first state, the beam engages the case detent or the carrier detent or both the case detent and the carrier detent.

8. The injection device according to claim 5, wherein, in the intermediate state, the beam engages the carrier detent, and the beam abuts the case.

9. The injection device according to claim 3, wherein, in the second state, the beam engages the case detent, and the beam abuts the carrier.

10. The injection device according to claim 1, wherein the carrier is adapted to accommodate a syringe such that the syringe is configured to jointly axially translate with the carrier.

11. The injection device according to claim 1, wherein, in the second state, the trigger button and the carrier move proximally relative to the case and the trigger button disengages the carrier and engages the case as the carrier, driven by a control spring, continues to move.

12. An injection device for administering a dose of a medicament, comprising:
   a case having a proximal end and a distal end;
   a carrier adapted to accommodate a syringe;
   and a trigger button,
   wherein the trigger button includes a deflectable beam adapted to engage the case and the carrier, the case includes a case detent adapted to engage the beam, the carrier includes a carrier detent adapted to engage the beam, and the beam includes a first ramp adapted to engage the carrier detent,
   wherein, in a first state, the trigger button is coupled to the case or the carrier or both the case and the carrier and abuts the distal end of the case such that the trigger button cannot be depressed in a proximal direction,
   wherein, in an intermediate state, the case moves proximally relative to the carrier and the trigger button causing the trigger button to protrude from the distal end of the case, and the trigger button engages the carrier, and
   wherein, in a second state, the trigger button and the carrier move proximally relative to the case and the trigger button disengages the carrier and engages the case.

13. The injection device according to claim 12, wherein the beam includes a second ramp adapted to engage the case detent.

14. The injection device according to claim 12, wherein, in the first state, the beam engages the case detent or the carrier detent or both the case detent and the carrier detent.

15. The injection device according to claim 12, wherein, in the second state, the beam engages the case detent, and the beam abuts the carrier.

16. The injection device according to claim 12, wherein, in the intermediate state, the beam engages the carrier detent, and the beam abuts the case.

17. The injection device according to claim 12, wherein, in the second state, the trigger button and the carrier move proximally relative to the case and the trigger button disengages the carrier and engages the case as the carrier, driven by a control spring, continues to move.

18. An injection device for administering a dose of a medicament, comprising:
   a case having a proximal end and a distal end;
   a carrier adapted to accommodate a syringe;
   and a trigger button,
   wherein the trigger button includes a deflectable beam adapted to engage the case and the carrier, the case includes a case detent adapted to engage the beam, and the carrier includes a carrier detent adapted to engage the beam,
   wherein, in a first state, the trigger button is coupled to the case or the carrier or both the case and the carrier and abuts the distal end of the case such that the trigger button cannot be depressed in a proximal direction,
   wherein, in an intermediate state, the case moves proximally relative to the carrier and the trigger button causing the trigger button to protrude from the distal end of the case, the trigger button engages the carrier, the beam engages the carrier detent, and the beam abuts the case, and
   wherein, in a second state, the trigger button and the carrier move proximally relative to the case and the trigger button disengages the carrier and engages the case.

19. The injection device according to claim 18, wherein the beam includes a first ramp adapted to engage the case detent and a second ramp adapted to engage the carrier detent.

20. The injection device according to claim 18, wherein in the first state, the beam engages the case detent or the carrier detent or both the case detent and the carrier detent, and in the second state, the beam engages the case detent and the beam abuts the carrier.

* * * * *